(12) United States Patent
Flores et al.

(10) Patent No.: US 11,224,524 B2
(45) Date of Patent: Jan. 18, 2022

(54) INTERBODY IMPLANT INSERTER

(71) Applicant: Spinal Elements, Inc., Carlsbad, CA (US)

(72) Inventors: Markanthony Flores, Chula Vista, CA (US); Kyle Elsabee, San Diego, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 274 days.

(21) Appl. No.: 16/420,667

(22) Filed: May 23, 2019

(65) Prior Publication Data

US 2019/0307579 A1 Oct. 10, 2019

Related U.S. Application Data

(62) Division of application No. 15/010,204, filed on Jan. 29, 2016, now Pat. No. 10,342,678.

(60) Provisional application No. 62/111,020, filed on Feb. 2, 2015.

(51) Int. Cl.
*A61F 2/46* (2006.01)
*A61F 2/44* (2006.01)
*A61F 2/30* (2006.01)

(52) U.S. Cl.
CPC ............ *A61F 2/4611* (2013.01); *A61F 2/447* (2013.01); *A61F 2/4603* (2013.01); *A61F 2002/30235* (2013.01); *A61F 2002/30263* (2013.01); *A61F 2002/30787* (2013.01); *A61F 2002/30878* (2013.01); *A61F 2002/30904* (2013.01)

(58) Field of Classification Search
CPC .................................................... A61F 2/4611
See application file for complete search history.

(56) References Cited

U.S. PATENT DOCUMENTS

| | | |
|---|---|---|
| 5,055,104 A | 8/1991 | Ray |
| 5,263,953 A | 11/1993 | Bagby |
| 5,489,307 A | 2/1996 | Kuslich et al. |
| 5,662,683 A | 9/1997 | Kay |
| 5,824,008 A | 10/1998 | Bolduc et al. |
| 5,885,299 A | 3/1999 | Winslow et al. |
| 6,056,749 A | 5/2000 | Kuslich |
| 6,066,175 A | 5/2000 | Henderson et al. |
| 6,113,637 A | 9/2000 | Gill et al. |

(Continued)

FOREIGN PATENT DOCUMENTS

| | | |
|---|---|---|
| WO | WO 2010/111802 | 10/2010 |
| WO | WO 2017/175024 | 10/2017 |

OTHER PUBLICATIONS

Invitation to Pay Additional Search Fees in International Application No. PCT/US2020/031581, dated Aug. 4, 2020.

(Continued)

*Primary Examiner* — Olivia C Chang
(74) *Attorney, Agent, or Firm* — Knobbe, Martens, Olson & Bear, LLP

(57) ABSTRACT

An implant holder is provided with a first guide lumen and second guide lumen. The implant holder has a first position wherein the implant holder couples to an interbody implant, aligns the first guide lumen with a first hole in the interbody implant, and aligns the second guide lumen with a second hole in the interbody implant. The implant holder has a second position wherein the implant holder releases the interbody implant.

9 Claims, 18 Drawing Sheets

(56) References Cited

U.S. PATENT DOCUMENTS

| | | |
|---|---|---|
| 6,156,037 A | 12/2000 | Le Huec et al. |
| 6,231,610 B1 | 5/2001 | Geisler |
| 6,276,883 B1 | 8/2001 | Unsworth et al. |
| 6,296,656 B1 | 10/2001 | Bolduc et al. |
| 6,432,106 B1 | 8/2002 | Fraser |
| 6,551,319 B2 | 4/2003 | Lieberman |
| 6,551,322 B1 | 4/2003 | Lieberman |
| 6,730,127 B2 | 5/2004 | Michelson |
| 6,896,676 B2 | 5/2005 | Zubok et al. |
| 6,953,462 B2 | 10/2005 | Lieberman |
| 6,984,234 B2 | 1/2006 | Bray |
| D524,443 S | 6/2006 | Blain |
| 7,056,341 B2 | 6/2006 | Crozet |
| 7,077,864 B2 | 7/2006 | Byrd, III et al. |
| 7,094,239 B1 | 8/2006 | Michelson |
| 7,112,222 B2 | 9/2006 | Fraser et al. |
| D533,277 S | 12/2006 | Blain |
| 7,172,627 B2 | 2/2007 | Fiere et al. |
| D539,934 S | 4/2007 | Blain |
| D541,940 S | 5/2007 | Blain |
| 7,601,167 B2 | 10/2009 | Liberman |
| 7,766,947 B2 | 8/2010 | Hawkes et al. |
| 7,850,731 B2 | 12/2010 | Brittan et al. |
| 7,935,123 B2 | 5/2011 | Fanger et al. |
| 8,100,955 B2 | 1/2012 | Blain et al. |
| 8,142,504 B2 | 3/2012 | Petit |
| 8,333,804 B1 | 12/2012 | Wensel |
| 8,394,107 B2 | 3/2013 | Fanger et al. |
| 8,500,811 B2 | 8/2013 | Blain et al. |
| 8,523,945 B1 | 9/2013 | Wensel |
| 8,740,983 B1 | 6/2014 | Arnold et al. |
| 8,801,785 B2 | 8/2014 | Brittan et al. |
| 8,808,304 B2 | 8/2014 | Weiman et al. |
| 8,840,668 B1 | 9/2014 | Donahoe et al. |
| 8,900,310 B2 | 12/2014 | Carlson et al. |
| 8,926,702 B2 | 1/2015 | Gorek et al. |
| 8,945,227 B2 | 2/2015 | Kirschman |
| 9,180,022 B2 | 11/2015 | Georges et al. |
| 9,375,237 B2 | 6/2016 | Keegan et al. |
| 9,750,616 B2 | 9/2017 | Blain et al. |
| 10,238,439 B2 | 3/2019 | Prybis et al. |
| 10,342,678 B2 | 7/2019 | Flores et al. |
| 10,675,156 B2 | 6/2020 | Blain et al. |
| 2002/0022845 A1 | 2/2002 | Zdeblick et al. |
| 2004/0254579 A1 | 12/2004 | Buhren et al. |
| 2004/0258502 A1 | 12/2004 | Unsworth et al. |
| 2005/0049593 A1 | 3/2005 | Duong et al. |
| 2006/0201289 A1 | 9/2006 | Davidson et al. |
| 2008/0140203 A1 | 6/2008 | Davis |
| 2008/0161925 A1 | 7/2008 | Brittan et al. |
| 2008/0300634 A1 | 12/2008 | Gray |
| 2009/0018592 A1 | 1/2009 | Pitbladdo |
| 2009/0030520 A1 | 1/2009 | Biedermann et al. |
| 2009/0275988 A1 | 11/2009 | Baynham |
| 2010/0228297 A1 | 9/2010 | Bray et al. |
| 2010/0256690 A1 | 10/2010 | Appenzeller et al. |
| 2010/0305704 A1 | 12/2010 | Messerli |
| 2011/0166660 A1 | 7/2011 | Laurence |
| 2011/0190892 A1 | 8/2011 | Kirschman |
| 2011/0230918 A1 | 9/2011 | Gorek et al. |
| 2011/0264152 A1 * | 10/2011 | Weiman .............. A61B 17/1757 606/86 R |
| 2012/0232597 A1 | 9/2012 | Saidha et al. |
| 2013/0079879 A1 | 3/2013 | Suh |
| 2013/0190874 A1 | 7/2013 | Glazer |
| 2013/0268008 A1 | 10/2013 | McDonough et al. |
| 2016/0296341 A1 | 10/2016 | Tatsumi |
| 2017/0224389 A1 | 8/2017 | Tatsumi |
| 2017/0325968 A1 | 11/2017 | Blain |
| 2019/0083270 A1 | 3/2019 | Milz et al. |
| 2020/0352739 A1 | 11/2020 | Ouidja et al. |

OTHER PUBLICATIONS

International Search Report and Written Opinion in International Application No. PCT/US2020/031581, dated Oct. 14, 2020.

* cited by examiner

INTERBODY IMPLANT INSERTER

INCORPORATION BY REFERENCE TO ANY PRIORITY APPLICATIONS

This application is a divisional of U.S. patent application Ser. No. 15/010,204, filed Jan. 29, 2016, which claims priority benefit to U.S. Provisional Patent Application No. 62/111,020, filed Feb. 2, 2015, the disclosures of which are hereby incorporated by reference herein in their entirety.

BACKGROUND

Field

Some embodiments described herein relate generally to systems and methods for performing spinal fixation. Specifically, the disclosure relates to implant inserter tools and drill guides, particularly those used for orthopedic procedures.

Description of the Related Art

Advancing age, as well as injury, can lead to degenerative changes in the bones, discs, joints, and ligaments of the spine, producing pain and instability. Under certain circumstances, alleviation of the problems can be provided by performing spinal fusion. Spinal fusion is a surgical technique in which two or more vertebrae of the spinal column are fused together to eliminate the motion between the fused vertebrae. Spinal fusion is used to treat conditions where the spine exhibits instability. Spine instability may result from causes such as fracture, scoliosis, and spondylolisthesis, where one or more vertebrae move in a forward direction relative to the other vertebrae. Spinal fusion with discectomy is also performed for herniation of the discs. This surgery involves removal of the affected disc and fusion of the adjacent vertebrae. Traditionally, bone grafts have been used to fuse the vertebrae, but various types of vertebral implants have also been used.

The use of intervertebral implants and bone screw fixation systems for treating injuries to bones is well established. In most instances, an intervertebral implant is positioned between adjacent vertebrae in the disc space and secured to the bone. The intervertebral implant can be secured to the bone by bone screws or other similar fasteners inserted through holes in the intervertebral implant and into the bone itself. The screws are tightened so that the intervertebral implant holds the bone to be treated in place in order to insure proper healing. Notwithstanding the foregoing, there remains a need for improved methods and devices for treating spinal instability.

SUMMARY

In some embodiments, an implant inserter is provided. The implant inserter can include a first portion, a second portion, and an engagement member disposed between the first portion and the second portion. The implant inserter can include a carrier coupled to the engagement member. The carrier can translate along the engagement member, as the engagement member is rotated, to move the first portion and the second portion between a first position to couple to an implant and a second position to release the implant.

The implant inserter can include the implant, wherein the implant includes a first hole and a second hole. In some embodiments, in the first position a first guide lumen of the first portion aligns with the first hole of the implant, and wherein in the first position a second guide lumen of the second portion aligns with the second hole of the implant. In some embodiments, the length of the implant measured from an anterior surface to a posterior surface is approximately equal to the length of the implant inserter. The implant inserter can include a handle coupled to the engagement member. The carrier can include one or more plates that are angled with respect to a longitudinal axis of the carrier. In some embodiments, the first portion comprises an angled catch that cooperates with the one of the plates of the carrier. In some embodiments, the second portion comprises an angled catch that cooperates with the one of the plates of the carrier. In some embodiments, as the engagement member is rotated, the first portion and the second portion move closer to clamp the implant between portions of the first portion and the second portion in the first position. In some embodiments, as the engagement member is rotated, the first portion and the second portion move apart to release the implant between portions of the first portion and the second portion in the second position. In some embodiments, the first portion and second portion comprise attachment arms to couple with complementary attachment sites on the implant. In some embodiments, the first portion comprises a first guide lumen and the second portion comprises a second guide lumen. In some embodiments, in the first position the first guide lumen aligns with a first hole of the implant and the second guide lumen aligns with a second hole of the implant. In some embodiments, the first hole and the first guide lumen form a linear trajectory. In some embodiments, the second hole and the second guide lumen form a linear trajectory. In some embodiments, the first hole and the first guide lumen form a first linear trajectory, wherein the second hole and the second guide lumen form a second linear trajectory, wherein the first linear trajectory and the second linear trajectory cross. In some embodiments, the first guide lumen guides a first fastener into a superior vertebra and the second guide lumen guides a second fastener into an inferior vertebra. In some embodiments, the length of the first fastener is approximately equal to the length of the first guide lumen. In some embodiments, at least one of the first portion or the second portion comprises a slot. In some embodiments, at least one of the first portion or the second portion comprises a stop.

In some embodiments, a method is provided for using an implant inserter comprising a first portion having a first guide lumen and a second portion having a second guide lumen. The method can comprise the step of translating the first portion of the implant inserter toward the second portion of the implant inserter to clamp an implant. In some embodiments, translating the first portion of the implant inserter toward the second portion of the implant inserter aligns the first guide lumen with a first hole of the implant and aligns the second guide lumen with a second hole of the interbody implant.

The method can comprise the step of implanting the implant with the implant inserter coupled thereto. The method can comprise the step of inserting a fastener through the first guide lumen, the first hole, and into a superior vertebra. The method can comprise the step of inserting a second fastener through the second guide lumen, the second hole, and into an inferior vertebra. The method can comprise the step of translating the first portion of the implant inserter away from the second portion of the implant inserter to release the implant after inserting the first fastener and the second fastener. The method can comprise the step of rotating an engagement member of the implant inserter to translate the first portion of the implant inserter away from the second portion of the implant inserter. The method can comprise the step of visualizing a trajectory through the first portion via a slot in the first portion. The method can comprise the step of visualizing a trajectory through the second portion via a slot in the second portion. The method can comprise the step of abutting a stop with an anatomical structure to limit the depth of insertion of the implant. The method can comprise the step of abutting a stop with a superior vertebra to limit the depth of insertion of the implant. The method can comprise the step of abutting a stop with an inferior vertebra to limit the depth of insertion of the implant.

In some embodiments, an advantage is that the interbody implant inserter stabilizes the interbody implant during the method step of securing the fasteners to the vertebral bodies. One possible advantage is that the implant holder and the handle can prevent migration of the interbody implant during a surgical procedure. Another possible advantage is that the implant holder and handle can facilitate the proper placement of the interbody implant within the intervertebral space. In some embodiments, an advantage is that the handle does not have to be removed during insertion of the fasteners. One possible advantage is that the implant holder is connected to the interbody implant during insertion of the interbody implant in the intervertebral space. Another possible advantage is that the implant holder stays connected to the interbody implant during insertion of the fasteners through the interbody implant. Another possible advantage is that the implant holder is only removed from the interbody implant after the one or more fasteners are through the interbody implant.

In some embodiments, an advantage is that the trajectory of tools through the interbody implant is more accurate. For instance, the trajectory of drills or biopsy needles through one or more holes in the interbody implant can be more accurate. In some embodiments, the trajectory of one or more fasteners through the interbody implant is more accurate. One possible advantage is that the interbody implant cannot migrate from the implant holder. Another possible advantage is that the implant holder is correctly positioned in relationship to one or more holes when the interbody implant is clamped. In some embodiments, the trajectory is aligned through the drill guides of the implant holder and holes in the interbody implant. One possible advantage is that the interbody implant inserter may eliminate errors in the trajectories. In some embodiments, an advantage is that the trajectory can be visualized through the drill guides. In some embodiments, an advantage is the implant holder comprises one or more slots to view an inside of a guide lumen as objects are guided through the drill guides.

In some embodiments, an advantage is that the drill guides of the implant holder can have shorter barrel lengths than other drill guides. One possible advantage is that shorter, low profile barrel lengths allow greater angles for the trajectories through the interbody implant. One possible advantage is that greater angle trajectories for the fasteners create a stronger connection between the fastener and the endplate of the vertebrae. Another possible advantage is that the greater angle trajectories can prevent the fastener from being deflected by the endplate. Another possible advantage is that greater angle trajectories may allow the fasteners to embed deeper within the vertebral body. In some embodiments, an advantage is that the shorter barrel lengths may allow procedures through smaller incisions. One possible advantage is that the procedure may be a minimally invasive procedure.

In some embodiments, an advantage is that the quick release connection between the handle and the implant holder allows for easy attachment or detachment. One possible advantage is improved imaging from x-rays or improved visualization. In some embodiments, an advantage is that the quick release connection between the implant holder and the implant allows for easy attachment or detachment. One possible advantage is the ability to remove the implant holder easily after the insertion of the fasteners. Another possible advantage is that the implant holder can clamp the sides of the interbody implant. One possible advantage is that there is no need for an attachment screw hole on implant.

In some embodiments, an advantage is that the interbody implant inserter can be used with an impact hammer. One possible advantage is that forces can be transmitted from the handle to a surface of the implant holder. One possible advantage is that force can be transmitted from the handle through the implant holder and to the interbody implant. In some embodiments, an advantage is that the interbody implant inserter reduces operating room time by not having to switch between the use of a separate inserter and implant holder. One possible advantage is the coupling of the interbody implant, the implant holder and the handle.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught or suggested herein without necessarily achieving other objects or advantages as may be taught or suggested herein.

All of these embodiments are intended to be within the scope of the invention herein disclosed. These and other embodiments will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

The structure and method of using the interbody implant inserter will be better understood with the following detailed description of embodiments, along with the accompanying illustrations, in which.

DETAILED DESCRIPTION

Figure 1:
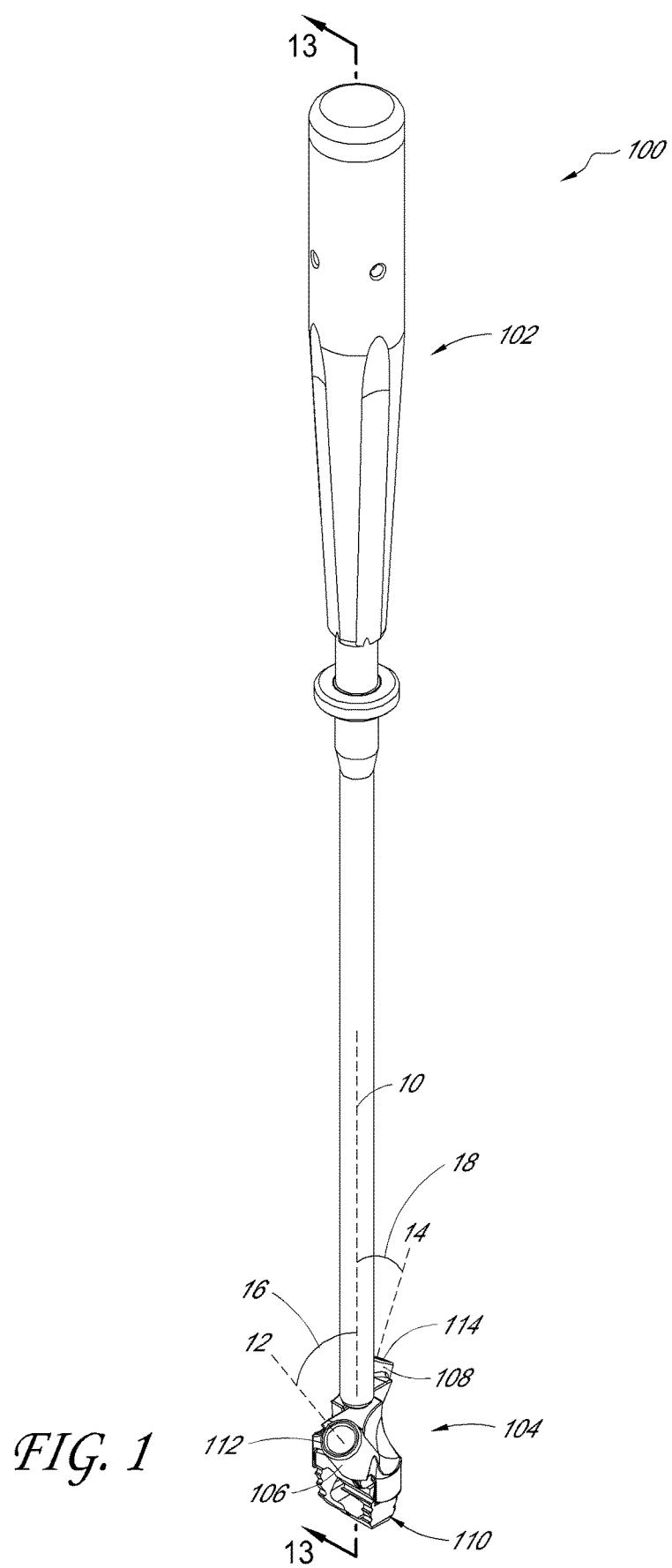
FIG. 1 is a perspective view of one embodiment of an interbody implant inserter.

Although certain preferred embodiments and examples are disclosed below, it will be understood by those in the art that the invention extends beyond the specifically disclosed embodiments and/or uses of the invention and obvious modifications and equivalents thereof. Thus, it is intended that the scope of the invention herein disclosed should not be limited by the particular disclosed embodiments described below.

Orthopedic devices such as interbody implants can be secured to a bone using fasteners inserted through the interbody implant. The insertion of the fasteners may be directed by drill guides for more precise placement, especially for surgical sites with limited access or visibility, such as the cervical spine. The success or failure of the interbody implant can often depend upon the precise placement of these fasteners. Interbody implants are typically delivered through a cannula. The preferred trajectory of the fasteners may be at an angle to the longitudinal axis of the cannula. Therefore, the walls of the cannula may impede access to or visibility of the preferred trajectory. In some embodiments, an interbody implant inserter is provided that facilitates the proper placement of fasteners. The interbody implant inserter can have additional functionality of facilitating the positioning of the interbody implant between the vertebra.

Although referred to as drill guides, these guides need not be used with actual drills but can be used for insertion of self-tapping or self-drilling fasteners, or to generally provide a guided pathway to a particular location for any of a number of purposes. For example, the drill guides can also facilitate access to the bone to perform a bone biopsy or for injection of drugs, cements or radiographic products.

A. Anatomy of the Spine

The vertebral column comprises a series of alternating vertebrae and fibrous discs that provide axial support and movement to the upper portions of the body. The vertebral column typically comprises thirty-three vertebrae, with seven cervical (C1-C7), twelve thoracic (T1-T12), five lumbar (L1-15), five fused sacral (S1-S5) and four fused coccygeal vertebrae. Each vertebra includes an anterior body with a posterior arch. The posterior arch comprises two pedicles and two laminae that join posteriorly to form a spinous process. Projecting from each side of the posterior arch is a transverse, superior and inferior articular process. The facets of the superior and inferior articular processes form facet joints with the articular processes of the adjacent vertebrae.

The typical cervical vertebrae differ from the other vertebrae with relatively larger spinal canals, oval shaped vertebral bodies, bifid spinous processes and foramina in their transverse processes. These foramina transversaria contain the vertebral artery and vein. The first and second cervical vertebrae also further differentiated from the other vertebrae. The first cervical vertebra lacks a vertebral body and instead contains an anterior tubercle. Its superior articular facets articulate with the occipital condyles of the skull and are oriented in a roughly parasagittal plane. The cranium is able to slide forward and backwards on this vertebra. The second cervical vertebra contains an odontoid process, or dens, which projects superiorly from its body. It articulates with the anterior tubercle of the atlas, forming a pivot joint. Side to side movements of the head occur at this joint. The seventh cervical vertebra is sometimes considered atypical since it lacks a bifid spinous process.

The typical lumbar vertebrae are distinguishable from the other vertebrae by the absence of foramina transversaria and the absence of facets on the surface of the vertebral body. The lumbar vertebral bodies are larger than the thoracic vertebral bodies and have thicker pedicles and laminae projecting posteriorly. The vertebral foramen is triangular in shape and larger than the foramina in the thoracic spine but smaller than the foramina in the cervical spine. The superior and inferior articular processes project superiorly and inferiorly from the pedicles, respectively.

The interbody implant described herein can be located at any level of the vertebral column. The interbody implant inserter can be used with an anterior cervical implant. The interbody implant inserter can be used with a lumbar implant. The interbody implant inserter can have various maximum widths to accommodate one or more implants. For instance, an interbody implant inserter can have a maximum width of 14 mm, an interbody implant inserter can have a maximum width of 16 mm, and an interbody implant inserter can have a maximum width of 18 mm. Two or more of the interbody implant inserters can be sold together as a kit. The two or more interbody implant inserters of one kit can have the same or different maximum widths. The interbody implant inserter can be produced as a kit with one or more corresponding implants. The interbody implant inserter can be produced as a kit with two or more interbody implant inserters. The interbody implant can be positioned between adjacent vertebra in the vertebral column. In the description herein, the interbody implant is described as positioned between a superior vertebra and an inferior vertebra. It should be appreciated that the interbody implant can be utilized in other portions of the spine other than between adjacent vertebra.

The orientation of the interbody implant can depend on the adjacent vertebra. For instance, the interbody implant can be parallel to the transverse plane. The interbody implant can be placed at any angle to the transverse plane, including parallel, substantially parallel, perpendicular, substantially perpendicular, 0 degrees, 15 degrees, 30 degrees, 45 degrees, 60 degrees, 75 degrees, 90 degrees, etc. The interbody implant 110 can be placed at any angle to the frontal plane, including parallel, substantially parallel, perpendicular, substantially perpendicular, 0 degrees, 15 degrees, 30 degrees, 45 degrees, 60 degrees, 75 degrees, 90 degrees, etc. The interbody implant inserter can facilitate placement of interbody implant within the vertebral column.

B. Interbody Implant Inserter

Figure 2:
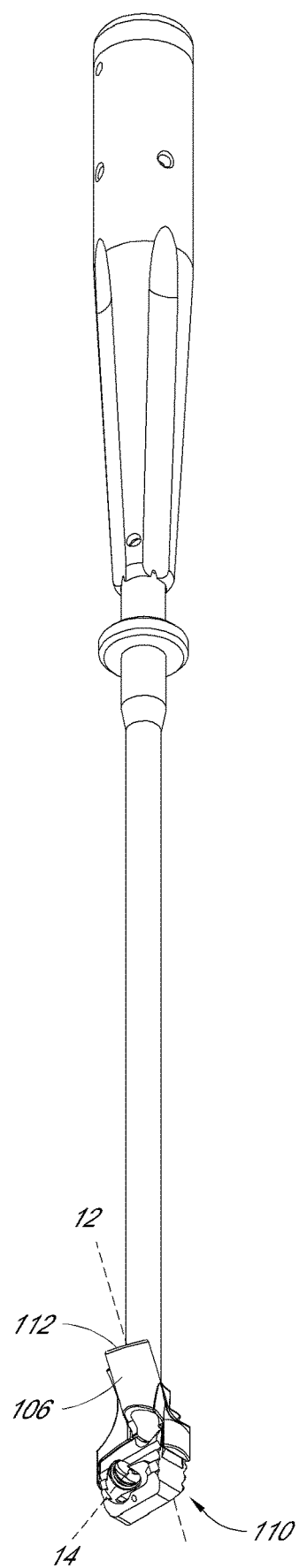
FIG. 2 is a perspective view of the interbody implant inserter of FIG. 1.

FIGS. 1 and 2 depict perspective views of an embodiment of an interbody implant inserter 100. As shown in FIGS. 1 and 2, the interbody implant inserter 100 can comprise a handle 102. The handle 102 can allow the user to manipulate the interbody implant inserter 100. The interbody implant inserter 100 can comprise an implant holder 104. The implant holder 104 can include a first portion 106 and a second portion 108 that can releasably hold an implant. In some embodiments, the first portion 106 can be identical or substantially similar to the second portion 108. In other embodiments, the first portion 106 is different than the second portion 108.

The interbody implant inserter 100 can couple with an interbody implant 110. The interbody implant 110 can be placed between the endplates of the superior and the inferior vertebra (not shown). In some embodiments, the interbody implant 110 can be secured to the superior vertebra, the inferior vertebra, or both the superior and inferior vertebra.

In some embodiments, the implant holder 104 includes one or more drill guides 112, 114. The interbody implant inserter 100 can facilitate placement of one or more fasteners. In some embodiments, each fastener is guided through the interbody implant 110 by the drill guides 112, 114. For instance, the first fastener can follow the trajectory 12 through the first drill guide 112 and the interbody implant 110. The trajectory 12 can form an insertion angle 16 relative to a central axis 10 of the interbody implant inserter 100. The second fastener can follow the trajectory 14 through the second drill guide 114 and the interbody implant 110. The trajectory 14 can form an insertion angle 18 relative to the central axis 10. The fasteners can facilitate fusion of the superior and the inferior vertebra.

1. Interbody Implant

Figure 3:
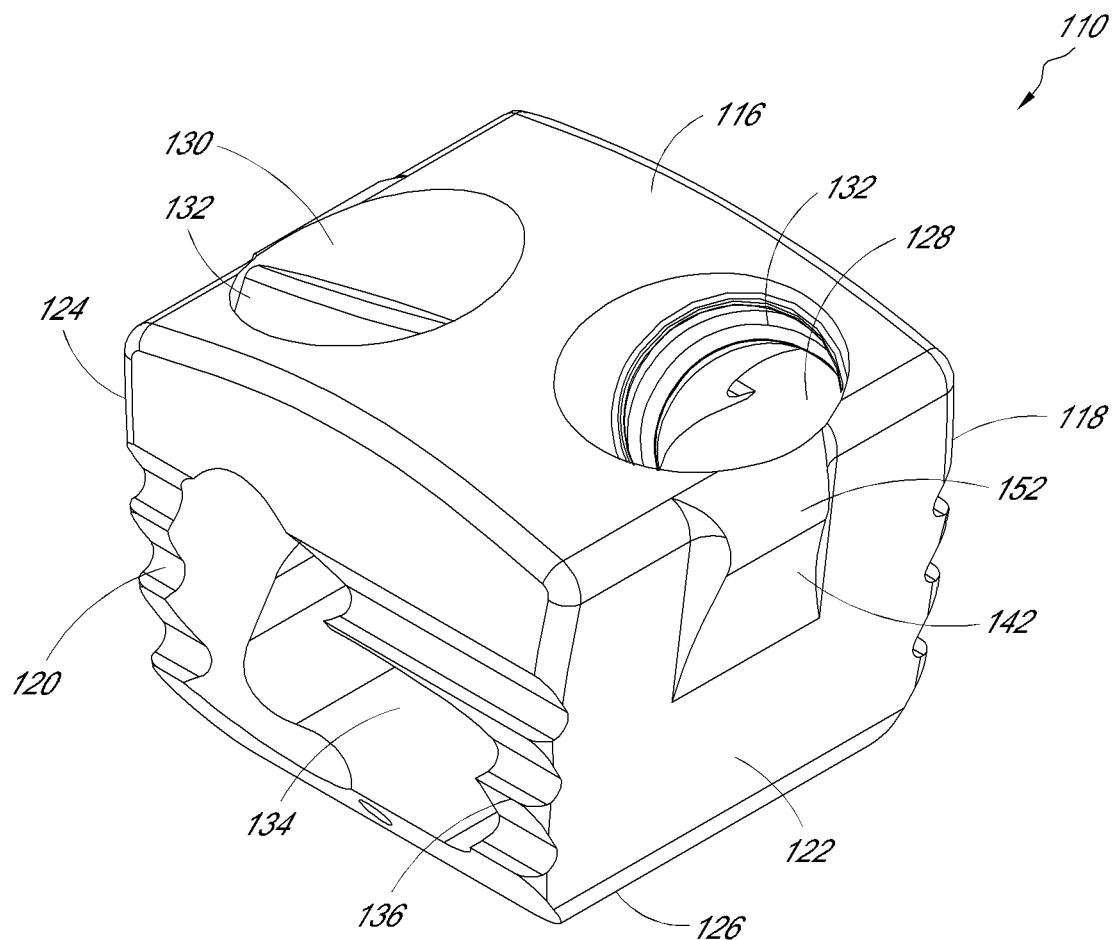
FIG. 3 is a perspective view of the interbody implant of FIG. 1.

FIG. 3 shows an embodiment of the interbody implant 110. The interbody implant 110 can comprise any structure configured to maintain a separation and resist compression between two adjacent vertebral bodies. The interbody implant 110 can have any of a variety of overall shapes, including but not limited to a rectangular box, a trapezoidal box, H-shaped, O-shaped, V-shaped, with or without one or more lumens within the interbody implant 110. As shown in FIG. 3, the interbody implant 110 can have an anterior surface 116, a superior surface 118 and an inferior surface 120, and side surfaces 122, 124, and a posterior surface 126. Each surface 118, 120, 122, 124, 126 need not be flat, and can be curved or undulating or any combination thereof. The superior and inferior surfaces 118, 120 can be configured for facing the superior and inferior vertebral bodies.

The anterior surface 116 can have a generally flat configuration, curved configuration or combination thereof. The edges of the anterior surface 116 can optionally be angled, rounded or curved. The edges of the anterior surface 116 can be smoothed or polished. In some embodiments, the anterior surface 116 of the interbody implant 110 can have a general square or rectangular shape. In other embodiments, the anterior surface 116 can comprise any of a variety of other shapes, including trapezoids, circles, ovals, polygons or other closed shapes. The anterior surface 116 is dimensioned to allow stable attachment of the fasteners to the adjacent vertebral bodies.

Referring to FIG. 3, the interbody implant 110 can have a first hole 128 and a second hole 130. The interbody implant 110 can have any number of holes, e.g., one, two, three, four, five, etc. The holes 128, 130 are configured to receive fasteners for anchoring the interbody implant 110 to one or more vertebrae. The holes 128, 130 can extend from the anterior surface 116 toward any other surface of the interbody implant (e.g., toward the superior surface 118, the inferior surface 120, the side surface 122, the side surface 124, the posterior surface 126, or any direction there between.). The holes 128, 130 can extend between any surface of the interbody implant 110. The holes 128, 130 may be oriented in different directions. For instance, the first hole 128 may be oriented toward the superior surface 118 and the second hole 130 may be oriented toward the inferior surface 120. The first hole 128 may receive the first fastener for securing the interbody implant 110 to the superior vertebra. The second hole 130 may receive the second fastener for securing the interbody implant 110 to the inferior vertebra. In other embodiments, the first hole 128 and the second hole 130 may be oriented toward the same surface.

Each hole 128, 130 need not have the same configuration or size. In some embodiments, the holes 128, 130 can be round in cross-sectional shape. The holes 128, 130 can comprise any of a variety of shapes including square, rectangular, trapezoids, circles, ovals, polygons or other closed shapes. In some embodiments, at least a portion of the holes 128, 130 can have a non-round cross-sectional shape. The holes 128, 130 can be dimensioned to allow passage of the body of the fastener while resisting passage of the head of the fastener. The inside surface of the holes 128, 130 can be covered with a lubricious coating to facilitate insertion and/or movement of the fasteners through the holes 128, 130. In some embodiments, a reinforcing member 132 is inserted into each hole 128, 130. In some embodiments, the reinforcing member 132 can reinforce the structural strength of the hole 128, 130. In some embodiments, the reinforcing member 132 can provide protection against wear on the hole 128, 130 by the fasteners. In some embodiments, the reinforcing member 132 can be made of a different material than the interbody implant 110. In some embodiments, the reinforcing member 132 can be formed of material such as metal including, but not limited to, titanium and its alloys, surgical grade plastics, plastic composites, ceramics, or other materials suitable for use as a spinal fusion implant. In some embodiments, the reinforcing member 132 can comprise a radiolucent material, a radio-opaque material, or a combination thereof.

The relative configuration of the superior surface 118 and the inferior surface 120 can vary, depending upon the relative position desired between the two adjacent vertebrae, the anatomical shape of the vertebrae, ease of insertion of the implant and other factors. For example, if a neutral vertical alignment is desired between two vertebrae, the superior and inferior surfaces 118, 120 can have generally parallel planar orientations. If a non-neutral alignment is desired, for instance to maintain a natural spinal curvature in the cervical region, the superior and inferior surfaces 118, 120 can have a wedge-like relationship to allow fixation of the vertebrae in the desired non-neutral position. A non-neutral alignment with respect to the anterior-posterior direction can also be used to compensate for excessive lordosis or kyphosis in other portions of the vertebral column. The height of the interbody implant 110 at any section between the superior and inferior surfaces 118, 120 can be further configured to accommodate degenerative changes or anatomical anomalies to provide fixation in the desired relative position. Likewise, the side surfaces 122, 124 of the interbody implant 110 can be generally parallel or skewed. In some embodiments, the side surfaces 122, 124 of the interbody implant 110 taper with increasing distance from the anterior surface 116 of the interbody implant 110.

A tapered interbody implant 110 can facilitate insertion of the interbody implant 110 into the intervertebral space. In other embodiments, the one or more side surfaces 122, 124 can flare distally or have both tapering and flaring portions.

FIG. 3 illustrates an embodiment of the interbody implant 110 comprising windows 134 between the superior and inferior surfaces 118, 120. In some embodiments, the interbody implant 110 comprises windows (not shown) between the side surfaces 122, 124. Other configurations are contemplated. The windows 134 can allow bony growth into the interbody implant 110. The windows 134 can also be filled with graft materials (not shown). The graft material can be an autograft, allograft, xenograft or synthetic material. Synthetic graft material can be ceramic-based, silicon-based or calcium-based. The graft material can also include osteoinductive factors to promote bone ingrowth. One skilled in the art will appreciate that there are many varieties of synthetic graft materials and constituents that can be used between or about the hyoid bone segments.

One or more surfaces of the interbody implant 110 can also have surface projections, indentations, or holes or pores that can further alter the characteristics of the interbody implant 110. Referring to FIG. 3, in some embodiments, the interbody implant 110 can include engagement features 136 designed to engage the adjacent anatomical features. The engagement feature 136 can include angled projections, barbs, teeth, or ramped surfaces which incline outwardly from one or more surface of the interbody implant 110. In some embodiments, the engagement features 136 are provided on the superior surface 118, the inferior surface 120 or both the superior and inferior surfaces 118, 120. Other surfaces of the interbody implant 110 can also include engagement features 136. In some embodiments, the engagement features 136 can be combined with indentations, holes or pores for allowing bony ingrowth which may enhance insertion and stabilization of the interbody implant 110.

The engagement features 136 can allow insertion of the interbody implant 110 in one direction but resist movement in the opposite direction. The engagement features 136 can be advantageous in reducing the migration of the interbody implant 110 out of the intervertebral space. The engagement features 136 can maintain the position of the interbody implant 110 during drilling of the pilot holes into the vertebral bodies or inserting the fasteners. The engagement features 136 can also reduce the forces acting upon the fasteners, thereby reducing the risk of backout.

In some embodiments, the interbody implant 110 can have a height between the superior surface 118 and the inferior surface 120 of about 4 mm to about 50 mm, or preferably about 4 mm to about 12 mm. In some embodiments, the interbody implant 110 can have a height of about 6 mm to about 9 mm. In some embodiments, the interbody implant 110 can have a length as measured from the anterior surface 116 to the posterior surface 126 of about 5 mm to about 25 mm. In some embodiments, length of the interbody implant 110 can be about 10 mm to about 15 mm. The width between the side surfaces 122, 124 of the interbody implant 110 can be generally about 5 mm to about 25 mm, and in some embodiments, about 10 mm to about 15 mm. One skilled in the art can dimension the interbody implant 110 based upon the implantation location and specific vertebral morphology, neurological anatomy and disease state.

The interbody implant 110 can include, be made of, treated, coated, filled, used in combination with, or contain artificial or naturally occurring materials suitable for implantation in the human spine. These materials can include any source of osteogenesis, bone growth-promoting materials, bone derived substances, bone morphogenetic proteins, hydroxyapatite, genes coding for the production of bone, and bone including, but not limited to, cortical bone. The interbody implant 110 can also be formed of material such as metal including, but not limited to, titanium and its alloys, surgical grade plastics, plastic composites, ceramics, or other materials suitable for use as a spinal fusion implant. In some embodiments, the interbody implant 110 can comprise a radiolucent material, a radio-opaque material, or a combination thereof. An interbody implant 110 that is partially or completely radiolucent can be advantageous when evaluating the effect of the interbody implant 110 post-implantation. Many existing interbody implants obscure visualization of the vertebrae, which can complicate post-operative treatment, diagnosis and prognosis of the patient's condition. The interbody implant 110 can include at least in part materials that are bioabsorbable in the body.

The interbody implant 110 of the described embodiments can be formed of a porous material or can be formed of a material that intrinsically participates in the growth of bone from one of adjacent vertebral bodies to the other of adjacent vertebral bodies. The interbody implant 110 can be treated with, coated with, or used in combination with substances to inhibit scar tissue formation. The interbody implant 110 can be modified, or used in combination with materials to provide antibacterial properties, such as, but not limited to, electroplating or plasma spraying with silver ions or other substance. The interbody implant 110 can optionally comprise an electrical source to provide ionophoresis of the silver ions into the surrounding tissue to prevent infection. The antibacterial properties can include bactericidal and/or bacteriostatic characteristics. Similarly, anti-fungal characteristics can also be provided. Any of these materials as appropriate can be used at any time after the interbody implant 110 is inserted.

2. Drill Guide

Referring back to FIGS. 1 and 2, the implant holder 104 can function to clamp the interbody implant 110. This provides a mechanical connection between the implant holder 104 and the interbody implant 110. In embodiments having drill guides 112, 114, the drill guides 112, 114 can function to guide fasteners through the interbody implant 110 along trajectories 12, 14. The trajectories 12, 14 guide the fasteners into the adjacent vertebral bodies. The drill guides 112, 114 can facilitate access to the holes 128, 130 of the interbody implant 110, as well as provide a guide for a particular trajectory to the holes 128, 130. The drill guides 112, 114 can facilitate the correct drilling or insertion angle for the fasteners through the holes 128, 130 of the interbody implant 110. This latter function may be useful for both fixed angle fasteners and polyaxial fasteners.

The interbody implant inserter 100 has many advantages. The implant holder 104 can stabilize the interbody implant 110 during the drilling or fastening method steps. The implant holder 104 can prevent migration of the interbody implant 110 while the fasteners are being inserted or pilot holes are being drilled. The interbody implant inserter 100 can form a single system that does not need to be removed from the surgical site to insert the fasteners. This can be advantageous over other systems having separate tools for insertion of the interbody implant and for guiding the fasteners. If using separate inserter and drill guide, the interbody implant can migrate in the intervertebral space after the inserter is removed and when the drill guide is being attached. The interbody implant inserter 100 can reduce operating room time. The surgeon does not need to switch between a separate inserter and drill guide.

The drill guides 112, 114 can have shorter barrel lengths and shorter guide lumens. The shorter, low profile barrel lengths can allow greater insertion angles for the trajectory 12, 14 of the fasteners. The insertion angles can be greater than drill guides that have longer barrels. The greater insertion angles 16, 18 create a stronger connection of the fasteners with the endplates of the adjacent vertebrae. Lesser insertion angles can cause a fastener to be deflected by the endplates and skim the surface of the endplate without embedding within the endplate. The low profile barrels of the drill guides 112, 114 can enable procedures through smaller incisions and minimally invasive procedures.

The trajectory of a tool such as a drill can be more accurate through the interbody implant 110 and into the adjacent bone. The trajectory of the fasteners can be more accurate. The drill guides 112, 114 can reduce errors in trajectories. With current tools, the interbody implants 110 can migrate in the intervertebral space after the inserter is removed and/or when the drill guide is attached. If using separate inserter and drill guide, the drill guide might not be positioned correctly, resulting in drill or screw trajectories that are not aligned with the screw holes in the implant.

a. Clamping Function

The implant holder 104 can detachably engage the interbody implant 110. As shown in FIGS. 4-7, the implant holder 104 may include one or more attachment sites 140 to facilitate attachment or engagement of the implant holder 104 to the interbody implant 110. The implant holder 104 comprises the first portion 106 and the second portion 108. Each of the first portion 106 and second portion 108 can include an attachment site 140.

The attachment sites 140 may engage one or more surfaces of the interbody implant 110. In some embodiments, the interbody implant 110 may include one or more complementary attachment sites 142 to facilitate the attachment and/or detachment of the implant holder 104. In some embodiments, the complementary attachment sites 142 are located on the side surfaces 122, 124. In other embodiments, the complementary attachment sites 142 are located on other surfaces of the interbody implant 110. The implant holder 104 can clamp the sides 122, 124 of the interbody implant 110. This can reduce the need for an attachment screw hole on the interbody implant 110. The surgeon may have to prepare the intervertebral space to accommodate the engagement sites 140 of the implant holder 104.

In the illustrated embodiment, the attachment sites 140 comprise a first flange 144 and a second flange 146. The first flange 144 extends from a posterior surface of the first portion 106 and the second flange 146 extends from a posterior surface of the second portion 108. The first flange 144 is shaped to engage the side surface 122 of the interbody implant 110. The second flange 146 is shaped to engage the side surface 124. The flanges 144, 146 can have a smaller height than the interbody implant 110. For instance, the first flange 144 can have a smaller dimension than the height of the side surface 122 and the second flange 146 can have a smaller dimension than the height of the side surface 124. The flanges 144, 146 can include a surface treatment to increase grip on the complementary attachment sites 142 of the interbody implant 110. For instance, the flanges 144, 146 can include a porous or roughened surface.

Figure 6:
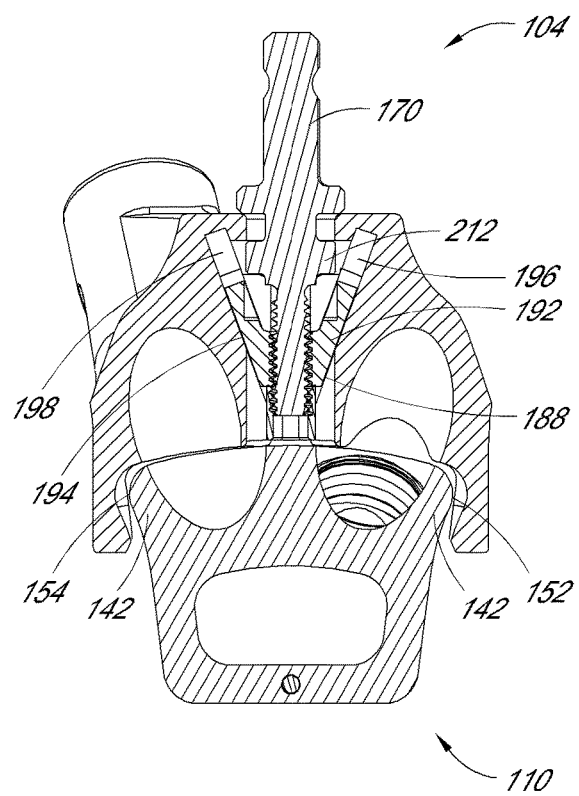
FIG. 6 is a cross-sectional view of the implant holder of FIG. 4 in a first position.
Figure 7:
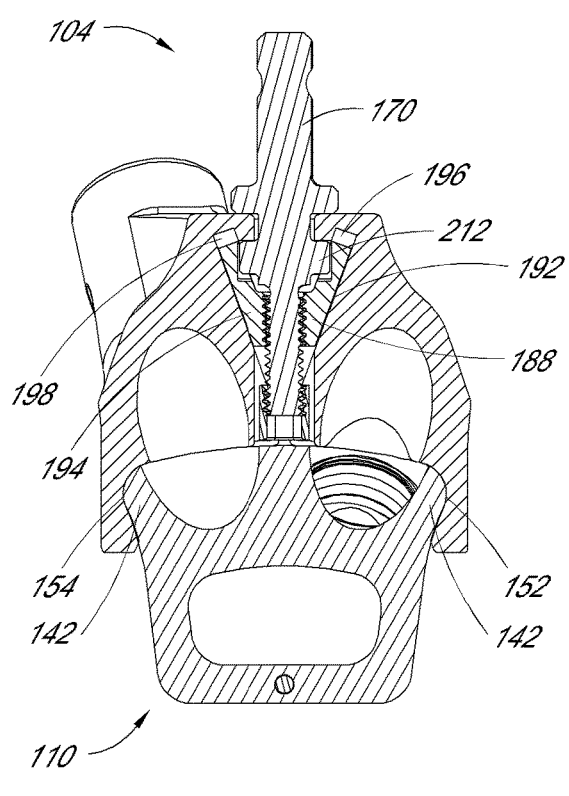
FIG. 7 is a cross-sectional view of the implant holder of FIG. 5 in a second position.

Referring to FIG. 6-7, the complementary attachment sites 142 comprise a first protrusion 152 and a second protrusion 154. The protrusions 152, 154 are generally of triangular shape as shown in FIG. 3. In other embodiments, the protrusions 152, 154 can be other shapes including polygonal, circular, oval, rectangular, etc. The complementary attachment sites 142 can have varying shapes, diameter, locations, and depth. The complementary attachment sites 142 can be located peripherally on the interbody implant 110. The complementary attachment sites 142 can be located near the anterior surface 116 of the interbody implant 110. In some embodiments, the complementary attachment sites 142 can comprise grooves that protrude into the side surfaces 122, 124 of the interbody implant 110.

Figure 4:
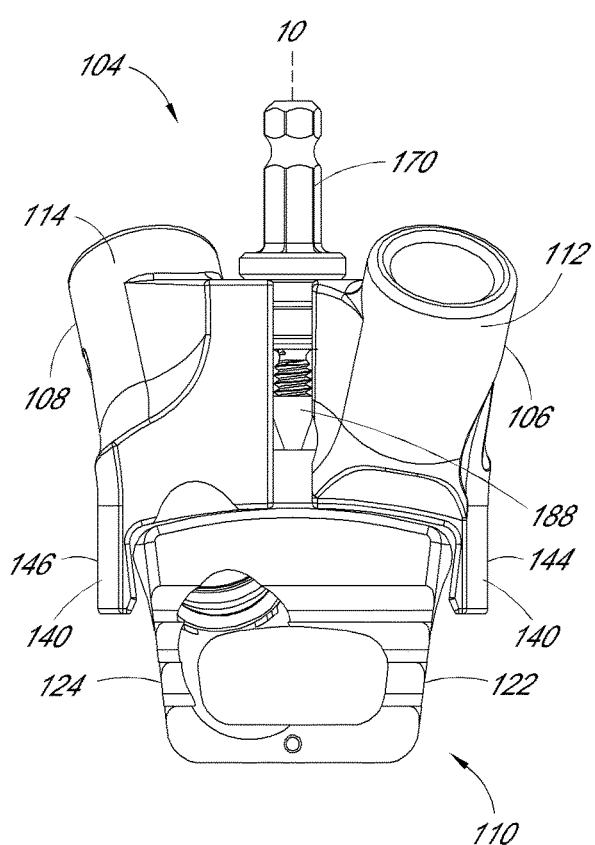
FIG. 4 is a front view of the implant holder of FIG. 1 in a first position.

In FIGS. 4 and 6, the interbody implant 110 can be placed between the attachment sites 140 of the implant holder 104. The attachment sites 140 are in alignment with the complementary engagement sites 142. In the illustrated embodiment, the first flange 144 of the first portion 106 is aligned with the first protrusion 152 on the side surface 122. The second flange 146 of the second portion 108 is aligned with the second protrusion 154 on the side surface 124. In the illustrated embodiment, the first portion 106 and the second portion 108 are moveable toward and away from each other. In some embodiments, the first portion 106 is moved toward the fixed second portion 108. In some embodiments, the second portion 108 is moved toward the fixed first portion 106. In some embodiments, all of the attachment sites 140 may be movable. In some embodiments, all of the complementary engagement sites 142 may be fixed.

Figure 5:
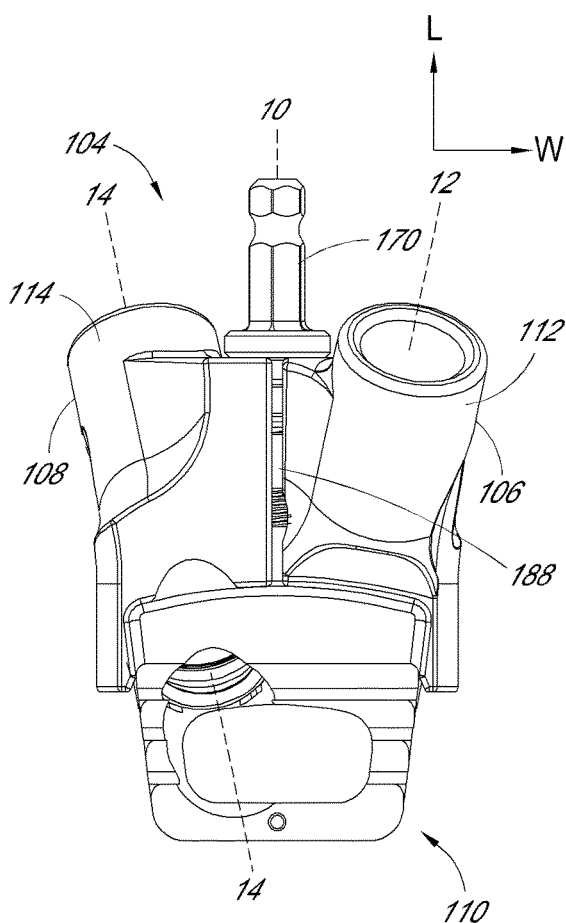
FIG. 5 is a front view of the implant holder of FIG. 1 in a second position.

By moving the first portion 106 and the second portion 108 as shown in FIGS. 5 and 7, the distance between the first flange 144 and the second flange 146 can decrease. The width of the implant holder 104 can decrease. The first flange 144 can substantially interlock with the protrusion 152 and the second flange 146 can substantially interlock with the protrusion 154. The shape of the flanges 144, 146 can limit the ability of the interbody implant 110 to disengage from the implant holder 104. The shape of the flanges 144, 146 can also facilitate centering the implant holder 104 with respect to the interbody implant 110. The flanges 144, 146 may slide on the protrusions 152, 154 until the width of the implant holder 104 can no longer be shortened.

The attachment sites 140 and the complementary attachment sites 142 can prevent movement of the interbody implant 110 relative to the implant holder 104 (e.g., in the posterior/anterior direction, in the superior inferior direction, etc.). In some embodiments, the attachment sites 140 and complementary attachment sites 142 serve to limit rotational movement between the interbody implant 110 and the implant holder 104, either during insertion of the interbody implant 110, or during insertion of the fasteners through drill guides 112, 114 and through the interbody implant 110. In other embodiments, the attachment sites 140 may have a cross-sectional shape that resists rotation with respect to the complementary attachment sites 142 on the interbody implant 110, e.g. a polygonal or oval shape.

In some embodiments, the attachment sites 140 and the complementary attachment sites 142 permit the coupling of the interbody implant 110 and the implant holder 104 in one or more preferred orientations. In the case of a symmetrical implant such as interbody implant 110, the attachment sites 140 and complementary attachment sites 142 permit the coupling of the interbody implant 110 and the implant holder 104 in one of two preferred orientation. For instance, the first flange 144 may couple to either protrusion 152, 154. The attachment sites 140 can be located at equal distances from the axis 10 on opposite sides of the implant holder 104.

In other embodiments, the attachment sites 140 and complementary attachment sites 142 may be dissimilar to allow coupling in a single orientation. For instance, the attachment sites 142 may be differently shaped. The attachment sites 140 can be located at equal or unequal distances from the axis 10 on opposite sides of the implant holder 104. For non-symmetrical interbody implants (not shown), each attachment sites 140 can correspond to a specific complementary attachment site 142.

In some embodiments, the attachment sites 140 and complementary attachment sites 142 may comprise, for example, any of a variety of complementary mechanical interfits, such as a threaded lock, snap-on fitting, or an interlocking fit. In some embodiments, the interfit may be a friction fit or a magnetic fit. In some embodiments, the attachment sites 140 may comprise a hook that engages a recess or pin on the interbody implant 110. In some embodiments, the attachment sites 140 may comprise a pivot or clamp member that retain the interbody implant 110 by grasping onto the sides of the interbody implant 110. As mentioned above, in some embodiments, the attachment sites 140 may be configured to generically couple to an interbody implant of a general size or shape and need not be specifically configured to each interbody implant. One of skill in the art will understand that any of a variety of disengageable mechanisms known in the art may be used to detachably couple the implant holder 104 to one or more interbody implants 110.

In some embodiments, the attachment sites 140 can comprise a threaded surface that engages a corresponding threaded lumen on the interbody implant 110. In some embodiments, in order to bring the corresponding threaded surfaces together, the first portion 106 and second portion 108 may be axially movable from an extended position to a retracted position. The attachment sites 140 may be movable rotationally until contact is made with the corresponding threaded lumen on the interbody implant 110. The attachment sites 140 and complementary attachment sites 142 may be freely positionable from its disengaged position to its engaged position. In some embodiments, the attachment sites 140 and complementary attachment sites 142 may be biased by a spring or other bias member in either position. In some embodiments, the implant holder 104 can provide tactile feedback to the user as to the current state between the implant holder 104 and the interbody implant 110.

As can be appreciated by one skilled in the art, the number and configurations of the attachment sites 140 and complementary attachment sites 142 provided on the drill guide 110 and the interbody implant 110 can vary. Other configurations are contemplated. In some embodiments, one or more attachment sites 140 or complementary attachment sites 142 may be removable to be removed, replaced, or substituted, depending upon the particular configurations of the interbody implant 110 being implanted.

b. Clamping Mechanism

Figure 8:
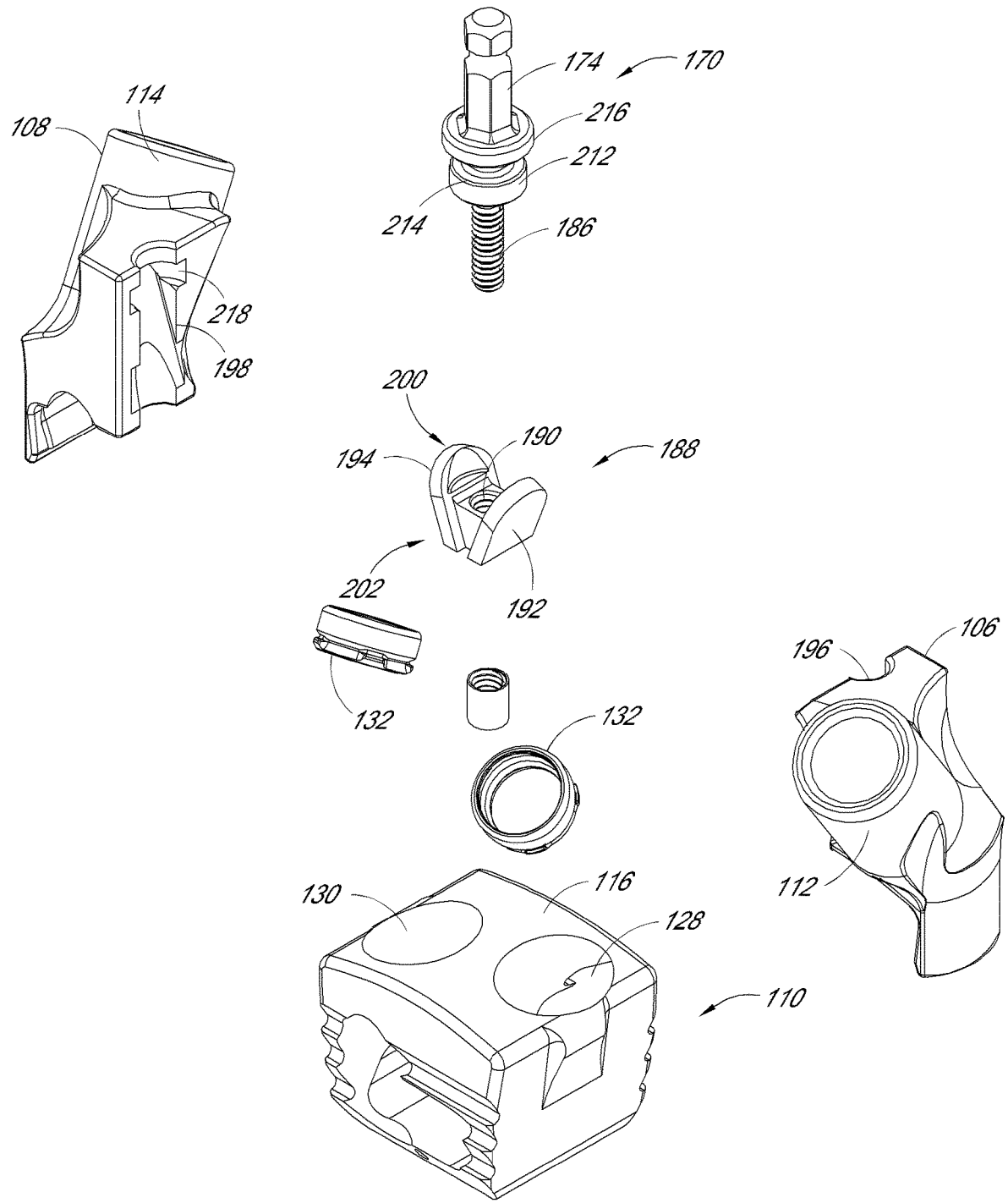
FIG. 8 is an exploded perspective view of the implant holder and interbody implant of FIG. 1.

FIGS. 6-8 depict an embodiment of the mechanism configured to move the first portion 106 and the second portion 108 of the implant holder 104. FIG. 6 depicts the implant holder 104 in the unclamped position. FIG. 7 depicts the implant holder 104 coupled to the interbody implant 110 in the clamped position. FIG. 8 depicts the implant holder 104 and the interbody implant 110 in an exploded view.

Referring to FIG. 8, the implant holder 104 comprises an engagement member 170. The engagement member 170 can include a threaded portion 186. In some embodiments, the threaded portion 186 is integrally formed with the engagement member 170. In some embodiments, the threaded portion 186 is a distal portion of the engagement member 170.

The implant holder 104 can include a carrier 188. The carrier 188 can include an internal threaded surface 190 configured to complement the threaded portion 186 of the engagement member 170. The carrier 188 is designed to travel longitudinally along the threaded portion of the engagement member 170 as the engagement member 170 is rotated. The carrier 188 can include a first plate 192 and a second plate 194. The first plate 192 and the second plate 194 can be angled with respect to the longitudinal axis of the internal threaded surface 190 such that a proximal portion 200 of the plates 192, 194 are farther apart than a distal portion 202 of the plates 192, 194. The first plate 192 can interact with the first portion 106 of the implant holder 104 and the second plate 194 can interact with the second portion 108 of the implant holder 104. The first plate 192 can be retained by a catch 196 of the first portion 106. The second plate 194 can be retained by a catch 198 of the second portion 108. The catch 196 can have an angled surface complementary to the angle of the first plate 192. The catch 198 can have an angled surface complementary to the angle of the second plate 194. When the carrier 188 is toward the distal end of the threaded portion 186 of the engagement member 170, the plates 192, 194 are retained by the distal portions of the catches 196, 198, and the distance between the first portion 106 and the second portion 108 of the implant holder 104 is greater. When the carrier 188 is toward the proximal end of the threaded portion 186 of the engagement member 170, the plates 192, 194 are retained by the proximal portions of the catches 196, 198, and the distance between the first portion 106 and the second portion 108 of the drill guide 104 is lesser. In some embodiments, the plates 192, 194 can retain the carrier 188 between the first portion 106 of the implant holder 104 and the second portion 108 of the implant holder 104.

The engagement member 170 can include a retention member 212. The retention member 212 can prevent longitudinal translation of the engagement member 170 when the engagement member 170 is rotated. In some embodiments, the retention member 212 includes a circular flange 214 disposed along the length of the engagement ember 170. The circular flange 214 of the engagement member 170 is received within complementary grooves 218 of the first portion 106 and the second portion 108. The circular flange 214 is sized to be rotationally received within the first portion 106 and the second portion 108. In some embodiments, the retention member 212 is integrally formed with the engagement member 170.

Referring back to FIGS. 4-7, the interbody implant 110 is positioned between the engagement sites 140 of the implant holder 104. The carrier 188 can be retained by the first portion 106 of the implant holder 104 and the second portion 108 of the implant holder 104. The proximal portion 200 of the plates 192, 194 can be retained by the catches 196, 198.

In some methods of use, the engagement member 170 is rotated. The threaded portion 190 of the carrier 188 can engage the threaded portion 186 of the engagement member 170. In a first configuration, the carrier 188 is located closer to the interbody implant 110. The carrier 188 can translate along the threaded portion 186 of the engagement member 170 while the retention member 212 prevents the engagement member 170 from translating.

The carrier 188 translates such that the proximal portion 200 and the distal portion 202 of the plates 192, 194 are retained by the catches 196, 198. In a second configuration, the carrier 188 is located further from the interbody implant 110. The plates 192, 194 can exert an inward force on the catches 196, 198. This force causes the distance between the first portion 106 and the second portion 108 to decrease. The distance between the engagement sites 140 of the implant holder 104 also decreases. Accordingly, the translation of the carrier 188 can cause the implant holder 104 to clamp the interbody implant 110.

The rotation of the engagement member 170 in the opposite direction can release the interbody implant 110. As the carrier 188 moves longitudinally along the engagement member 170 toward the interbody implant 110, the distance between the first portion 106 and the second portion 108 increases. The distance between the engagement sites 140 of the implant holder 104 also increases. The movement of the carrier 188 can cause the implant holder 104 to release the interbody implant 110.

c. Alignment Function

The drill guides 112, 114 can function to guide fasteners through the interbody implant 110. FIGS. 9-12 depict the implant holder 104 coupled to the interbody implant 110. The aligned coupling between the attachment sites 140 and complementary attachment sites 142 facilitates placement of a first guide lumen 158 and a second guide lumen 160. In particular, the first guide lumen 158 of the first drill guide 112 is aligned with the first hole 128 of the interbody implant 110 when the interbody implant 110 is clamped. The second guide lumen 160 of the second drill guide 114 is aligned with the second hole 130 of the interbody implant 110 when the interbody implant 110 is clamped. This alignment facilitates the placement of the fasteners through the holes 128, 130.

Referring to FIGS. 9-12, the guide lumens 158, 160 each include a proximal opening 162, distal opening 164, and a lumen there between. The distal opening 164 or a portion thereof may be flat or substantially flat to correspond to the shape of the anterior surface 116 of the interbody implant 110. The guide lumens 158, 160 may have a tubular configuration. The guide lumens 158, 160 may comprise any shape suitable for accurately guiding a drilling device or other instrument, or fastener. The guide lumens 158, 160 may be linear or non-linear. In the illustrated embodiment, the guide lumens 158, 160 are linear. Non-linear, linear or flexible tools including drills, screw drivers and biopsy needles are known in the art and may be used in conjunction with the guide lumens 158, 160.

In addition to the guide lumens 158, 160 illustrated in FIGS. 9-12, non-cylindrical lumens are also contemplated, including non-circular tubular lumens, frustoconical lumens, and others. The shape of the guide lumens 158, 160 can depend on the shape of the fastener, such as the shape of the head of the fastener. The guide lumens 158, 160 need not be circumferentially enclosed, and in some embodiments may have a trough-like configuration or have a seam along the length of the guide lumens 158, 160.

Figure 9:
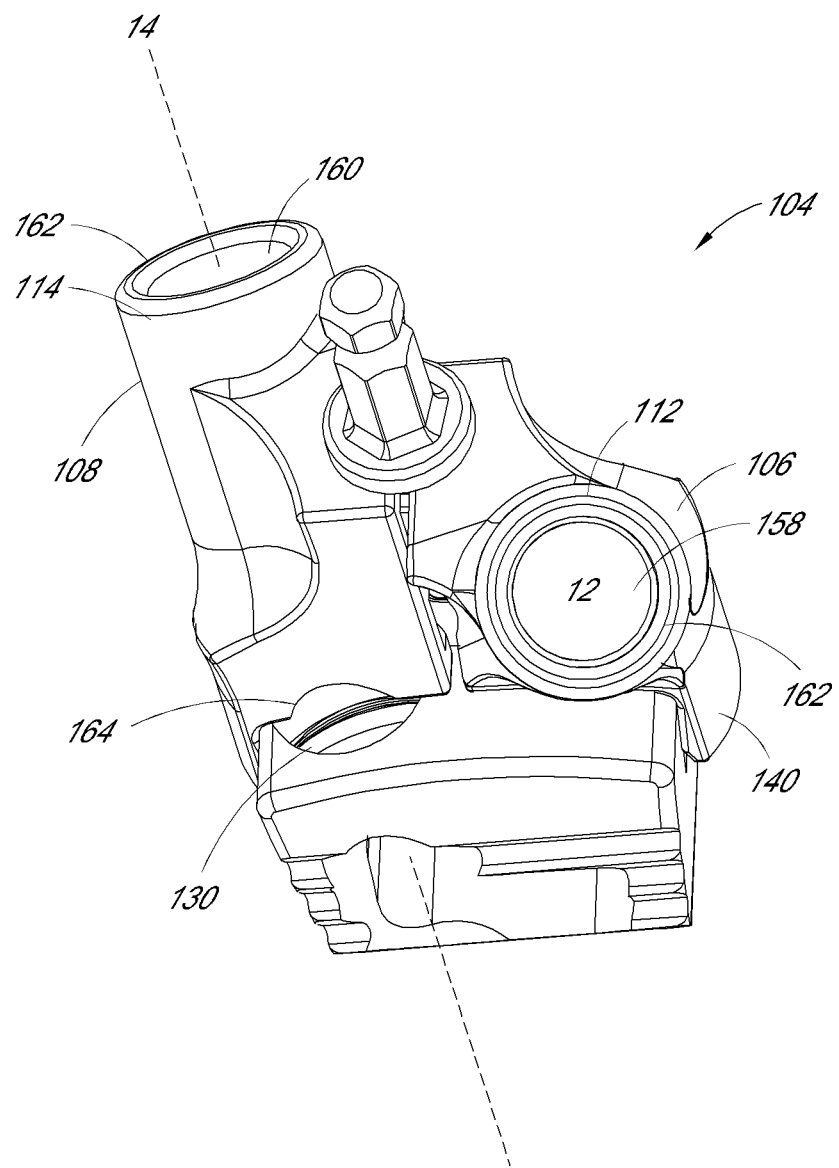
FIG. 9 is a perspective view of the implant holder and interbody implant.
Figure 10:
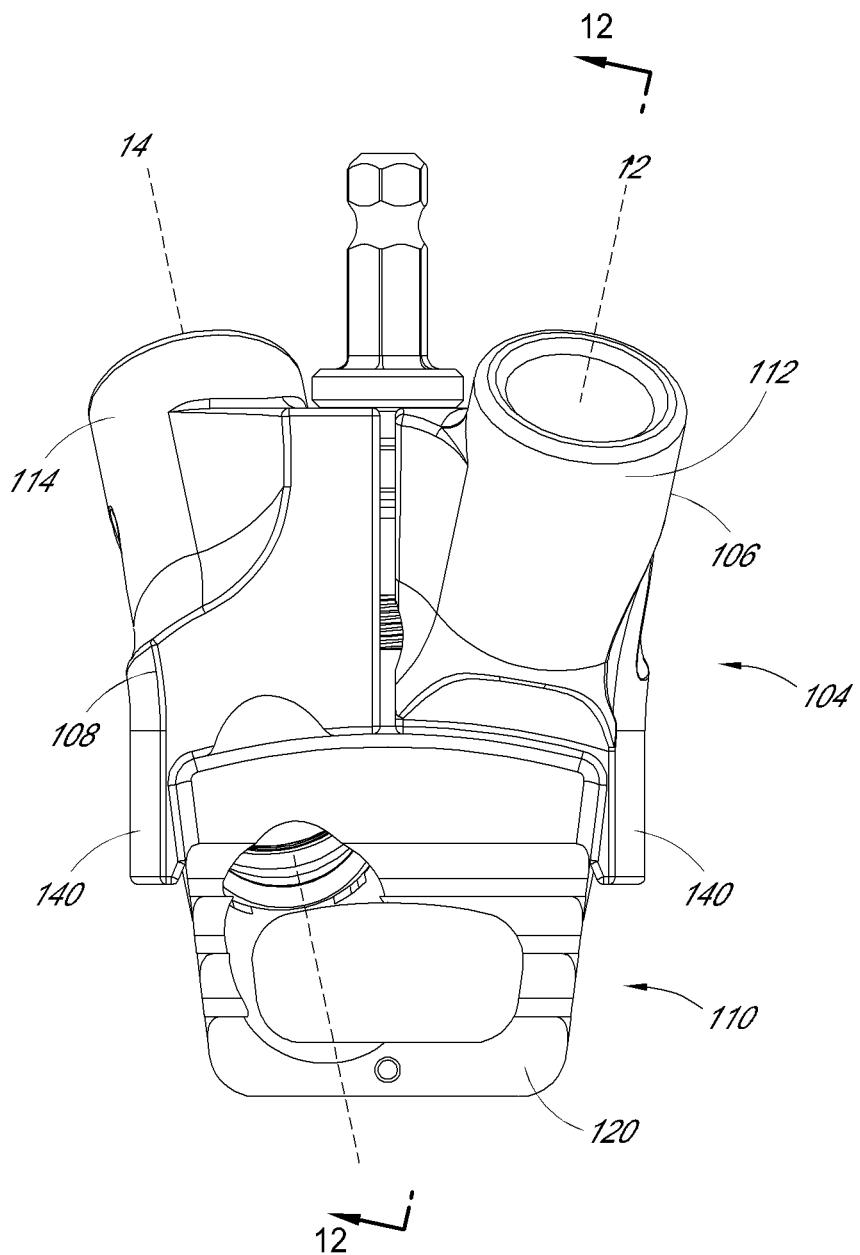
FIG. 10 is a front view of the implant holder and interbody implant of FIG. 1.

Although FIG. 9 depicts two guide lumens 158, 160, the implant holder 104 may comprise fewer or greater number of guide lumens (e.g., one, three, four, etc.). The number of guide lumens may correspond to the number of holes on the interbody implant 110. For instance, in the illustrated embodiment, the interbody implant 110 has two holes 128, 130 and the implant holder 104 includes two guide lumens 158, 160. In other embodiments, the number of guide lumens is less than or greater than the number of holes on the interbody implant 110. In one example, a drill guide (not shown) with four guide lumens may be provided but used with interbody implant with fewer than four holes. In some embodiments where the drill guide has a fewer number of guide lumens than the interbody implant (not shown), the drill guide may be rotatable to permit repositioning of the guide lumens 158, 160 with respect to the interbody implant 110.

FIG. 9 is a perspective view of the implant holder 104 and the interbody implant 110 showing the alignment of the guide lumens 158, 160 and the holes 128, 130. This alignment permits the user to insert instruments or fasteners into the guide lumens 158, 160 without potential interference from the interbody implant 110. After the interbody implant 110 is positioned in its desired location and orientation within the vertebral column, one or more fasteners may be inserted into the proximal openings 162 of the guide lumens 158, 160. For instance, a fastener can be inserted into the guide lumen 158 and through the first hole 128 of the interbody implant 110. The fastener can secure the interbody implant 110 to the superior vertebra. Another fastener can be inserted into the guide lumen 160 and through the second hole 130 of the interbody implant 110. The fastener can secure the interbody implant 110 to the inferior vertebra. In some methods of use, the fasteners are self-drilling or self-tapping. In other methods of use, a drill, screw driver or other insertion instrument is utilized to drive the fastener into bone.

Figure 11:
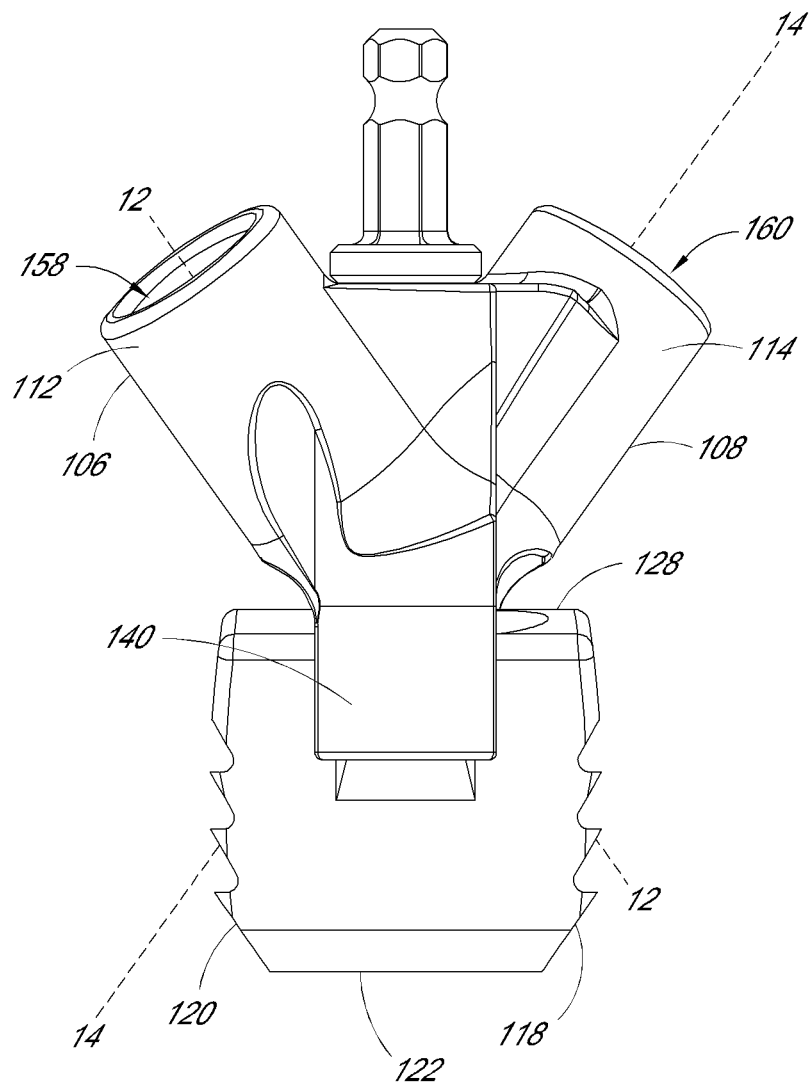
FIG. 11 is a side view of the implant holder and interbody implant of FIG. 1.

In the illustrated embodiment, the first portion 106 and the second portion 108 are identical or substantially similar in shape. In the illustrated embodiment, the first portion 106 is rotated 180 degrees relative to the second portion 108. The guide lumens 158, 160 are identical or substantially similar in shape. As shown in FIG. 11, the first portion 106 is oriented closer to the inferior surface 120 and the second portion 108 is oriented close to the superior surface 118. This orientation allows the guide lumen 158 of the first portion 106 to guide the fastener along the trajectory 12 through the superior surface 118 of the interbody implant 110. This orientation allows the guide lumen 160 of the second portion 108 to guide the fastener along the trajectory 14 through the inferior surface 120 of the interbody implant 110. In some embodiments, the two guide lumens 158, 160 may be similar in location and/or orientation relative to the interbody implant 110.

In some embodiments, the implant holder 104 can have a height approximately twice the height of the interbody implant 110. For instance, the implant holder 104 can have a height about 8 mm to about 100 mm. In some embodiments, the implant holder 104 can have a height of about 8 mm to about 24 mm or 12 mm to about 18 mm. In some embodiments, the implant holder 104 can have a lumen length as measured from the proximal opening 162 to the distal opening 164 of about 5 mm to about 25 mm. In some embodiments, the length of the implant holder 104 can be about 10 mm to about 15 mm. The width of the implant holder 104 between the engagement sites 140 can generally be equal to the width of the interbody implant 110. The width can be generally about 5 mm to about 25 mm, and in some embodiments, about 10 mm to about 15 mm. One skilled in the art can dimension the implant holder 104 based upon the interbody implant 110 and the trajectory of the fasteners.

d. Visualization Function

Figure 14:
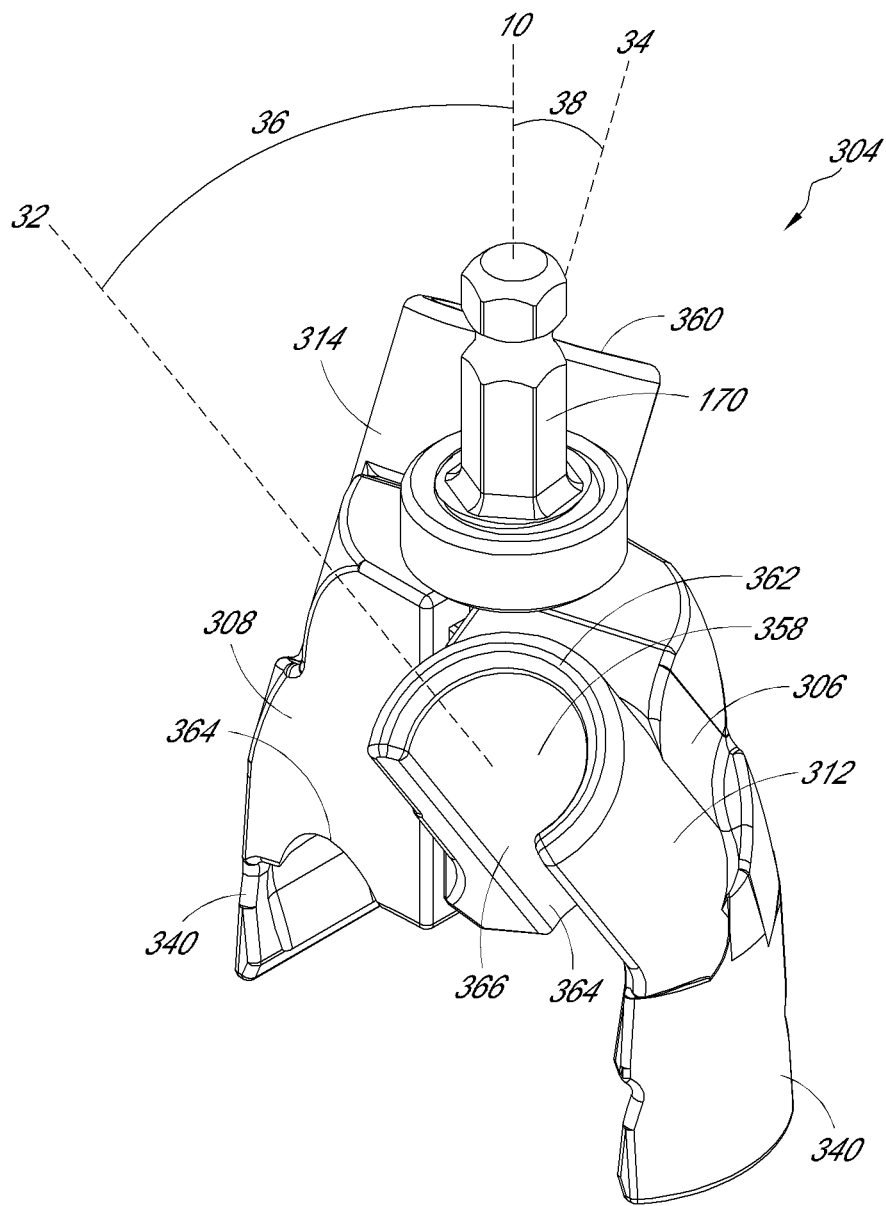
FIG. 14 is a perspective view of an embodiment of an implant holder.
Figure 15:
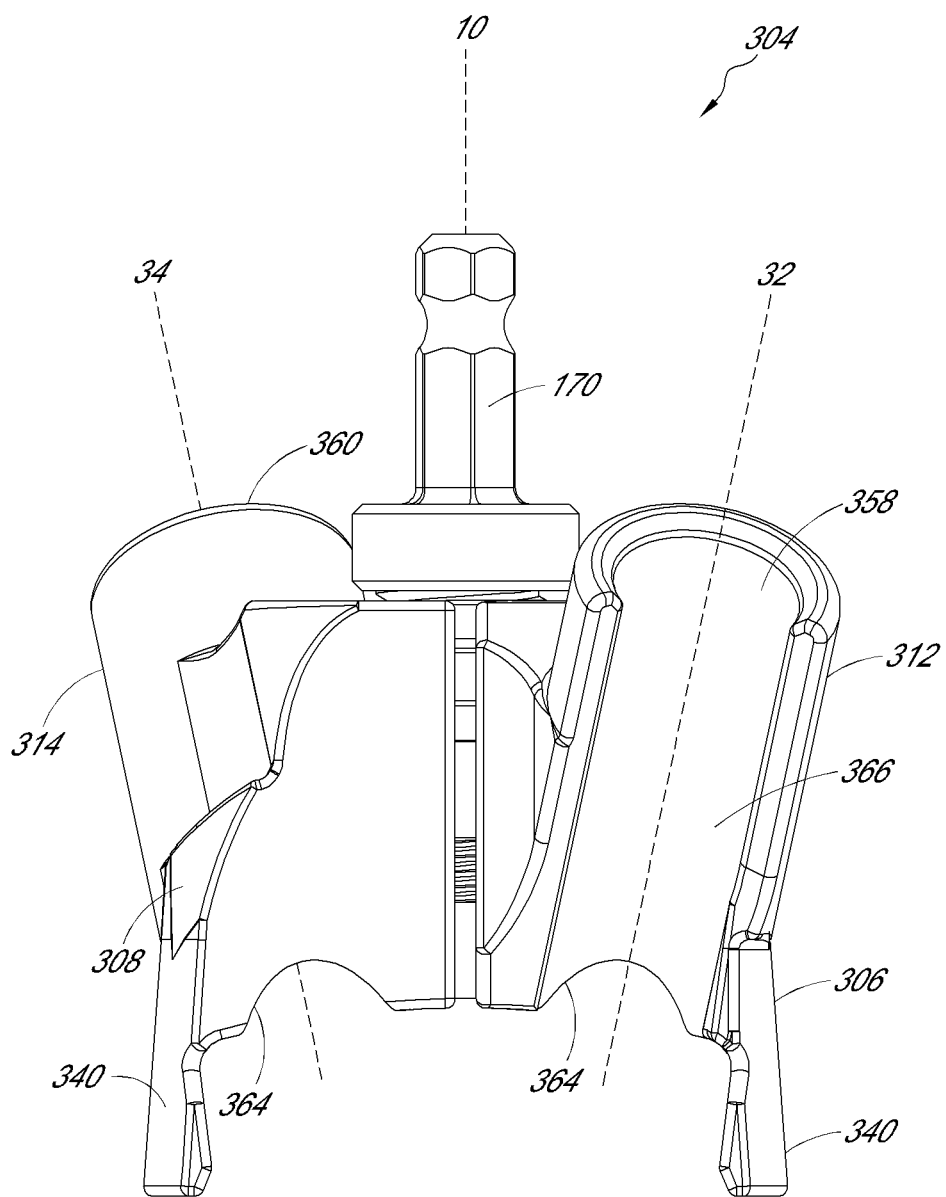
FIG. 15 is a front view of the implant holder of FIG. 14.
Figure 16:
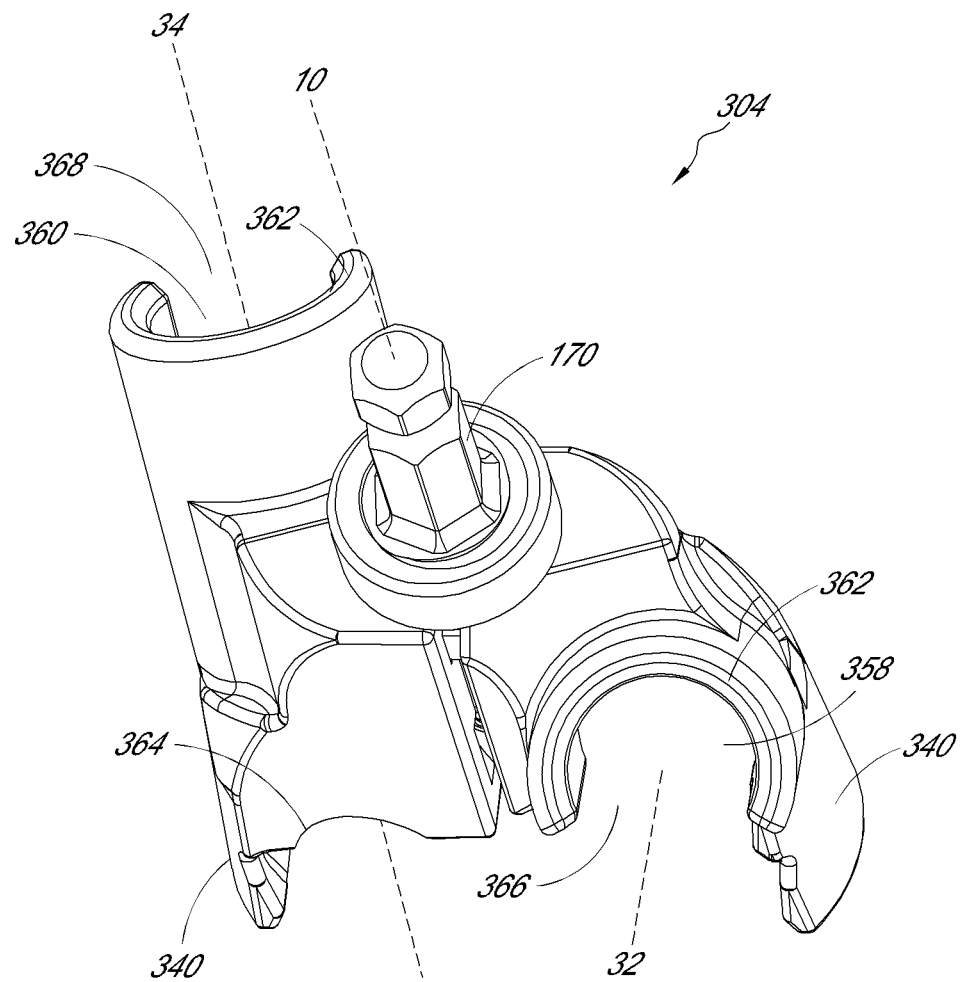
FIG. 16 is a perspective view of the implant holder of FIG. 14.
Figure 17:
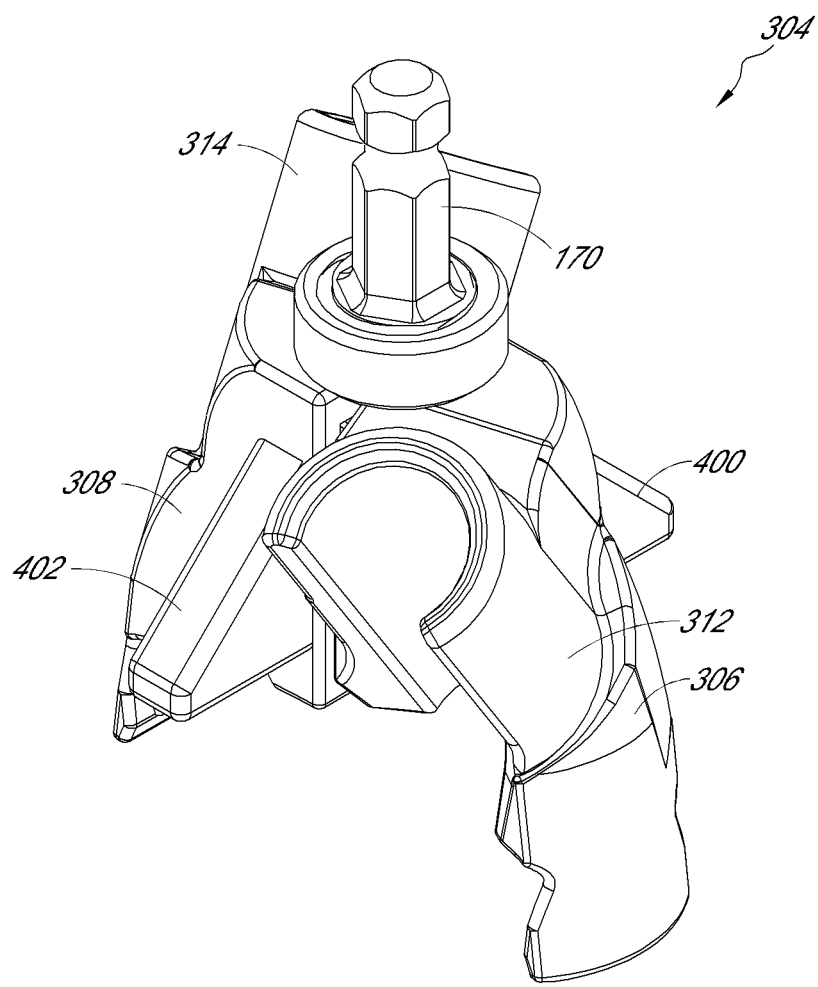
FIG. 17 is a perspective view of the implant holder of FIG. 14 including one or more stops.
Figure 18:
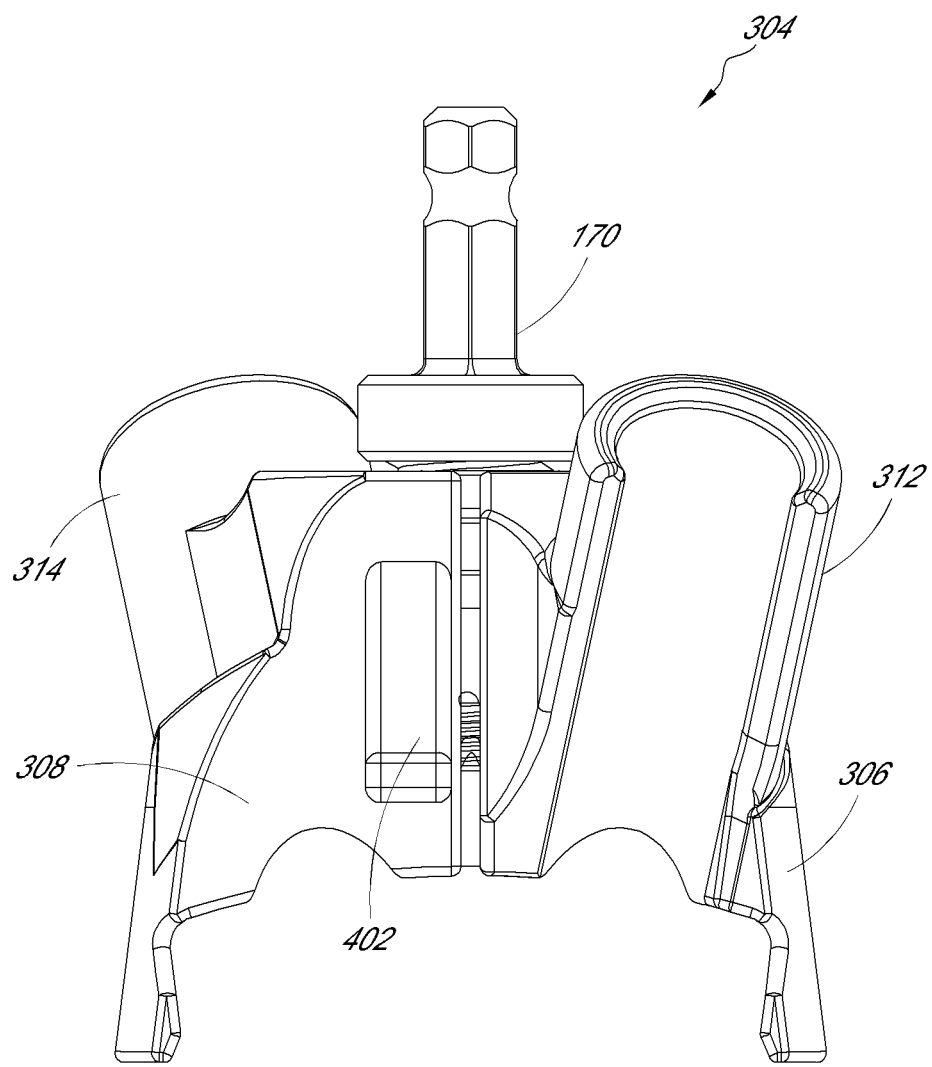
FIG. 18 is a front view of the implant holder of FIG. 17.
Figure 19:
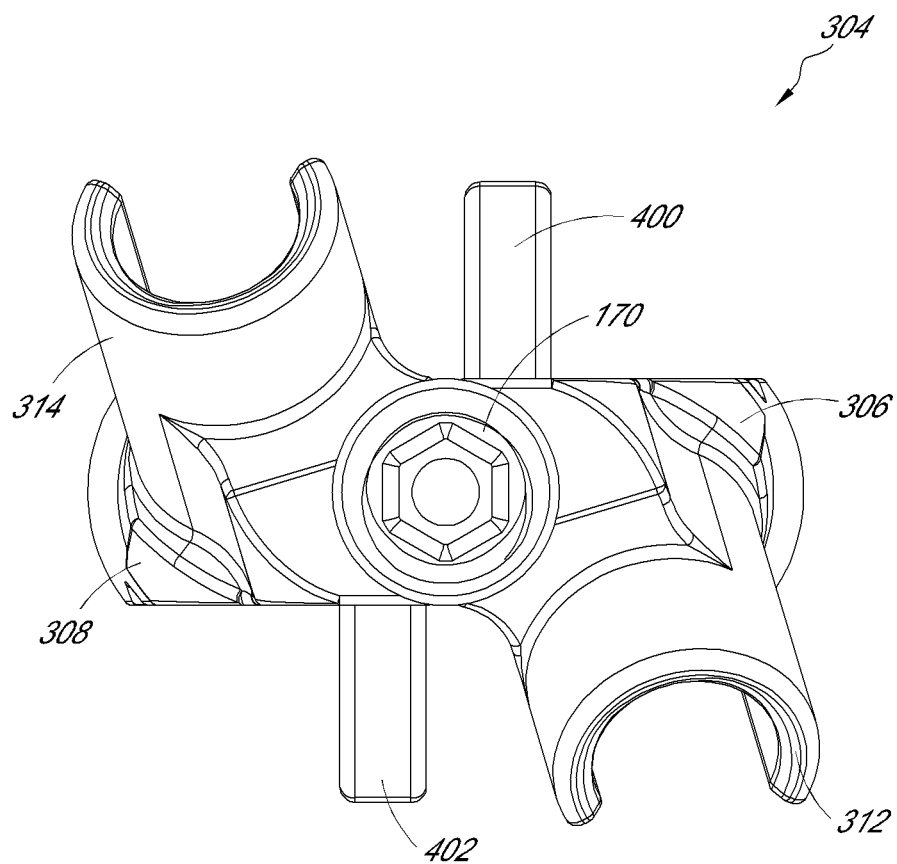
FIG. 19 is a top view of the implant holder of FIG. 17.

FIGS. 14-16 show an embodiment of an implant holder 304. The implant holder 304 can function in a similar manner to the implant holder 104, as described herein. The implant holder 304 can have similar features to the implant holder 104, as described herein, with the exception of differences described herein.

In some embodiments, the implant holder 304 includes one or more drill guides 312, 314. In some embodiments, each fastener is guided through the interbody implant 110, shown in FIG. 3, by the drill guides 312, 314. For instance, the first fastener can follow the trajectory 32 through the first drill guide 312 and the interbody implant 110 shown in FIG. 3. The trajectory 32 can form an insertion angle 36 relative to a central axis 10 of the interbody implant inserter 100, shown in FIG. 1. The second fastener can follow the trajectory 34 through the second drill guide 314 and the interbody implant 110. The trajectory 34 can form an insertion angle 38 relative to the central axis 10. The fasteners can facilitate fusion of the superior and the inferior vertebra.

The implant holder 304 may include one or more attachment sites 340 to facilitate attachment or engagement of the implant holder 304 to the interbody implant 110. The implant holder 304 can comprise a first portion 306 and a second portion 308. Each of the first portion 306 and the second portion 308 can include an attachment site 340. The aligned coupling between the attachment sites 340 and complementary attachment sites 142 of the interbody implant 110, shown in FIG. 3, facilitates placement of a first guide lumen 358 and a second guide lumen 360. In particular, the first guide lumen 358 of the first drill guide 312 is aligned with the first hole 128 of the interbody implant 110, shown in FIG. 3, when the interbody implant 110 is clamped. The second guide lumen 360 of the second drill guide 314 is aligned with the second hole 130, shown in FIG. 3, of the interbody implant 110 when the interbody implant 110 is clamped. This alignment facilitates the placement of the fasteners through the holes 128, 130, shown in FIG. 3 in a desired trajectory for engagement with the superior or inferior vertebra.

Referring to FIGS. 14-16, the guide lumens 358, 360 each include a proximal opening 362, distal opening 364, and a lumen there between. The distal opening 364 or a portion thereof can have a surface with a contour that corresponds to the shape of the anterior surface 116 of the interbody implant 110, shown in FIG. 3. For example, the distal opening or a portion thereof can be flat or substantially flat to correspond to an interbody implant having a flat or substantially flat anterior surface.

The drill guide 312 can include a slot 366. The drill guide 314 can include a slot 368. Each drill guide 312, 314 can include any number of slots 366, 368, e.g., zero, one, two, three, four, five, etc. The slots 366, 368 can extend distally from the proximal openings 362. The slots 366, 368 can extend proximally from the distal openings 364. The slots 366, 368 can extend between the proximal openings 362 and the distal openings 364, as shown in FIGS. 14-16. The slots 366, 368 can extend for any portion of the length of the drill guides 312, 314.

The guide lumens 358, 360 may have a semi-tubular configuration. The guide lumens 358, 360 may comprise any shape suitable for accurately guiding a device, such as a tool, drilling device, other instrument, or fastener. The guide lumens 358, 360 may be linear or non-linear. In the illustrated embodiment, the guide lumens 358, 360 are linear. Non-linear, linear, or flexible tools including drills, screw drivers and biopsy needles are known in the art and may be used in conjunction with the guide lumens 358, 360.

The slots 366, 368 can extend for a portion of the perimeter of the drill guides 312, 314. The slots 366, 368 can extend for a portion of the circumference of the drill guides 312, 314 if the drill guides are cylindrical. The slots 366, 368 can extend approximately 5% of the perimeter, 10% of the perimeter, 15% of the perimeter, 20% of the perimeter, 25% of the perimeter, 30% of the perimeter, 35% of the perimeter, 40% of the perimeter, 50% of the perimeter, ⅓ of the perimeter, ⅙ of the perimeter, ⅑ of the perimeter, etc. The configuration of the slots 366, 368 can hold objects captive within the guide lumens 358, 360. The configuration of the slots 366, 368 can prevent the passage of objects through the slots 366, 368, wherein the objects include fasteners and tools inserted within the drill guides 312, 314. In some embodiments, the slots 366, 368 are designed to be narrower than commonly used fasteners and tools. In other embodiments, the slots 366, 368 are designed to be wider than commonly used fasteners and tools to allow such fasteners and tools to enter the drill guides 312, 314 from the slot 366, 368 instead of the proximal openings 362. The slots 366, 368 can be straight, tapered, non-linear, curved, or any other configuration. The slots 366, 268 can ensure that any object inserted within the drill guides 312, 314 are inserted at the desired angle 36, 38 along the trajectories 32, 34. The trajectories 32, 34 can guide the fasteners into the adjacent vertebral bodies.

The slots 366, 368 visually open the drill guide 312, 314 such that a user can view the trajectories 32, 34 of objects inserted therewithin. The slots 366, 368 provide better visualization for inserting objects, including fasteners and tools, through the drill guides 312, 314. The slots 366, 368 facilitate the user's ability to perform functions through the drill guides 312, 314 including the actions of awling, drilling, tapping, and fastening. The visualization can ensure that the fasteners are inserted securely into the vertebrae. The visualization can ensure that the fasteners are inserted along the trajectories 32, 34.

Figure 12:
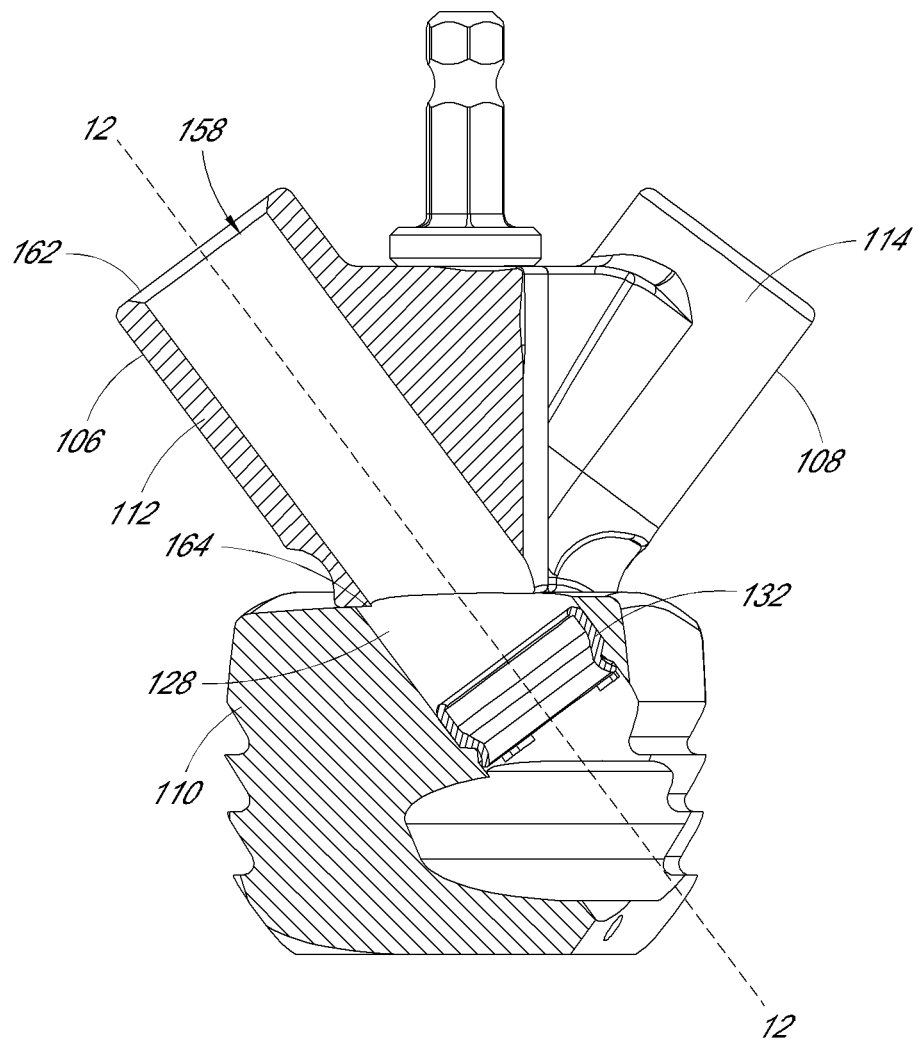
FIG. 12 is a cross-sectional view of the implant holder and interbody implant of FIG. 10 along line 12-12.

The drill guides 312, 314 can facilitate access to the holes 128, 130 of the interbody implant 110, as shown in FIG. 3, as well as provide a guide for a particular trajectory to the holes 128, 130, as shown in FIGS. 9 and 12. The slots 366, 368 can allow the user to see a fastener as the fastener is passed through the implant holder 304. The drill guides 312, 314 can facilitate the correct drilling or insertion angle for the fasteners through the holes 128, 130 of the interbody implant 110, as shown in FIG. 3. This latter function may be useful for both fixed angle fasteners and polyaxial fasteners.

The short, low profile barrel lengths of the drill guides 312, 314 can allow greater insertion angles for the trajectory 32, 34. The insertion angles can be greater than drill guides that have longer barrels. The greater insertion angles 36, 38 can create a stronger connection of the fasteners with the endplates of the adjacent vertebrae. The low profile barrels of the drill guides 312, 314 can enable procedures through smaller incisions and minimally invasive procedures.

In the illustrated embodiment, the first portion 306 and the second portion 308 are identical or substantially similar in shape. In the illustrated embodiment, the first portion 306 is rotated 180 degrees relative to the second portion 308. The guide lumens 358, 360 are identical or substantially similar in shape. The slots 366, 368 are identical or substantially similar in shape. Other configurations are contemplated.

e. Depth Function

FIGS. 17-21 show an embodiment of the implant holder 304 including one or more stops 400, 402. One or more stops 400, 402 can be utilized with the implant holder 104 or the implant holder 304 described herein. FIGS. 17-21 show the stops 400, 402 coupled with the implant holder 304. In some embodiments, one stop 400, 402 is coupled to the implant holder 104, 304. In other embodiments, two or more stops 400, 402 are coupled to the implant holder 104, 304 (e.g., two stops, three stops, four stops, five stops, six stops, etc.). In FIG. 17-21, the stop 400 is coupled with the first portion 306 and the stop 402 is coupled with second portion 308. In some embodiment, the stops 400, 402 are identical or substantially similar in shape. In the illustrated embodiment, the stop 400 is rotated 180 degrees relative to the stop 402. In other embodiments, the stops 400, 402 have different configurations. The stops 400, 402 can be shaped to correspond to the surrounding anatomy, as described herein. Other configurations are contemplated.

Figure 20:
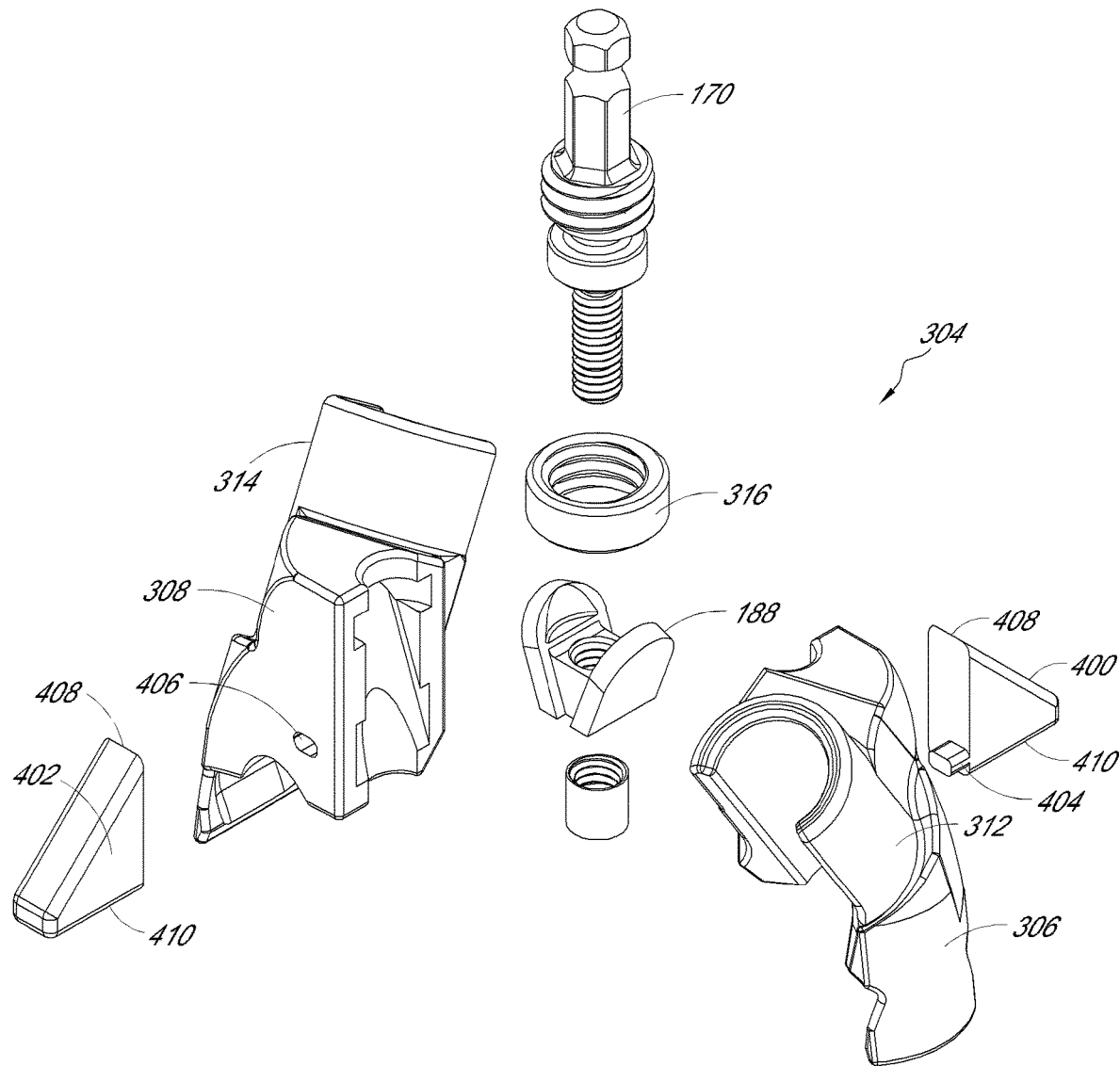
FIG. 20 is an exploded perspective view of the implant holder of FIG. 17.

The stops 400, 402 can be secured to the implant holder 104, 304. In some embodiments, the stops 400, 402 are removable, as shown in FIG. 20. The stops 400, 402 can be secured to the implant holder 104, 304 by a retaining member 404. The retaining member 404 can be a post. The implant holder 104, 304 can have a complementary retaining member 406. The complementary retaining member 406 can be a slot. In other embodiments, the retaining member 404 is a slot and the complementary retaining member 406 is a post. The retaining member 404 and the complementary retaining member 406 can be any configuration to allow the coupling of the stops 400, 402 and the implant holder 104, 304.

The retaining member 404 and the complementary retaining member 406 can have a non-circular geometry to prevent rotation of the stops 400, 402 relative to the implant holder 104, 304. In some embodiments, the complementary retaining member 406 can accept the retaining member 404 in a single orientation. In other embodiments, the complementary retaining member 406 can accept the retaining member 404 in two or more orientations. The complementary retaining member 406 can be located on the implant holder 104, 304 near the distal end of the first portion 106, 306 or the second portion 108, 308. In some embodiments, the retaining member 404 of the stops 400, 402 are identical or substantially similar in shape. The two complementary retaining members 406 can be identical or substantially similar to receive either retaining member 404. In other embodiments, the stops 400, 402 have different retaining members 404. The two complementary retaining members 406 can be different to receive one of the two retaining members 404.

The stop 400 can include a proximal end 408 and a distal end 410. In some embodiments, the retaining member 404 can be located near the proximal end 408 of stops 400, 402. In some embodiments, the retaining member 404 can be located near the distal end 410 of stops 400, 402. The stops 400, 402 can be triangular in shape. Other configurations are contemplated including tubular, rectangular, square, spherical, conical, etc. In some embodiments, the distal end 410 has a greater height than the proximal end 408 when coupled to the implant holder 104, 304. The height of the interbody implant 110 is measured between the superior and inferior surfaces 118, 120 as shown in FIG. 11. The height of the system including the stops 400, 402 is measured in this direction when the implant holder 104, 304 is coupled to the interbody implant 110.

The distal end 410 of the stop 400 can extend beyond the superior surface 118 of the interbody implant 110 when the implant holder 104, 304 is coupled to the interbody implant 110. The distal end 410 of the stop 400 can be configured to abut the superior vertebra. The distal end 410 of the stop 402 can extend beyond the inferior surface 120 of the interbody implant 110 when the implant holder 104, 304 is coupled to the interbody implant 110. The distal end 410 of the stop 402 can be configured to abut the inferior vertebra. The distal ends 410 of the stops 400, 402 can be designed to abut an adjacent vertebra. Other configurations are contemplated.

The stops 400, 402 limit the depth of insertion of the interbody implant 110 within the disc space between adjacent vertebrae. The user can insert the interbody implant 110 into the disc space until one or more stops 400, 402 abut an adjacent surface. The stop 400 can abut a superior vertebra or other anatomical structure, as described herein. The stop 402 can abut an inferior vertebra or other anatomical structure, as described herein. The abutment of one or more stops 400, 402 limits further insertion of the interbody implant 110 within the disc space.

The position of the distal end 410 of the stop 400, 402 can be selected based on the desired depth of insertion of the interbody implant 110. In some embodiments, the stop 400 can be selected from a plurality of stops based upon the desired depth of insertion, the anatomy of the patient, or other considerations. In some embodiments, the stop 402 can be selected from a plurality of stops. The distance between the posterior surface 126 of the interbody implant 110, shown in FIG. 3, and the distal end 410 of one or more stops 400, 402 can be equivalent to the desired distance between the posterior surface 126 of the interbody implant 110 and the surface of the adjacent vertebra.

In some embodiments, the position of the distal end 410 of the stop 400, 402 can be adjusted. In some embodiments, one or more stops 400, 402 can include a mechanism to raise and/or lower the distal end 410. In the context of adjustment of the distal end 410 of the stop 400, 402, raising and/or lowering means moving in the distal-proximal direction. In other embodiments, the retaining member 404 of one or more stops 400, 402 is adjustable relative to the one or more stops. The retaining member 404 can be raised and/or lowered relative to the distal end 410. In other embodiments, one or more of the complementary retaining member 406 of the implant holder 104, 304 is adjustable relative to the implant holder. The complementary retaining member 406 can be raised and/or lowered relative to the distal opening 164 of the drill guides 112, 114; 312, 314. In some embodiments, the stops 400, 402 can be infinitely adjustable within two end points. In other embodiments, the stops can be adjustable along incremental steps.

In the absence of one or more stops 400, 402, the interbody implant 110 can be inserted until an outer surface of the drill guides 112, 114; 312, 314 abut an anatomical feature. The one or more stops 400, 402 limit the depth of insertion to the distal surfaces 410 of the stops 400, 402. The one or more stops 400, 402 can provide a consistent depth of insertion of the interbody implant 110. The one or more stops 400, 402 can limit the depth of insertion regardless of the size or shape of the implant holder 104, 304 or the interbody implant inserter 100. The one or more stops 400, 402 can limit the depth of insertion regardless of any design or manufacturing tolerances. The one or more stops 400, 402 can limit the depth of insertion regardless of the placement of the drill guides 112, 114; 312, 314 relative to the adjacent anatomical features. The abutment of one or more stops 400, 402 can provide tactile feedback that the interbody implant 110 has achieved the desired depth of insertion. Abutment of one stop 400, 402 but not another stop 400, 402 can provide feedback that the interbody implant 110 may be inserted at an angle relative to the superior or inferior vertebrae. For instance in a system with two stops 400, 402 as shown in FIGS. 17-20, abutting only one stop 400 can indicate that the interbody implant 110 is tilted toward the inferior vertebra. For instance in a system with two stops 400, 402 as shown in FIGS. 17-20, abutting only one stop 402 can indicate that the interbody implant 110 is tilted toward the superior vertebra.

3. Handle

Figure 13:
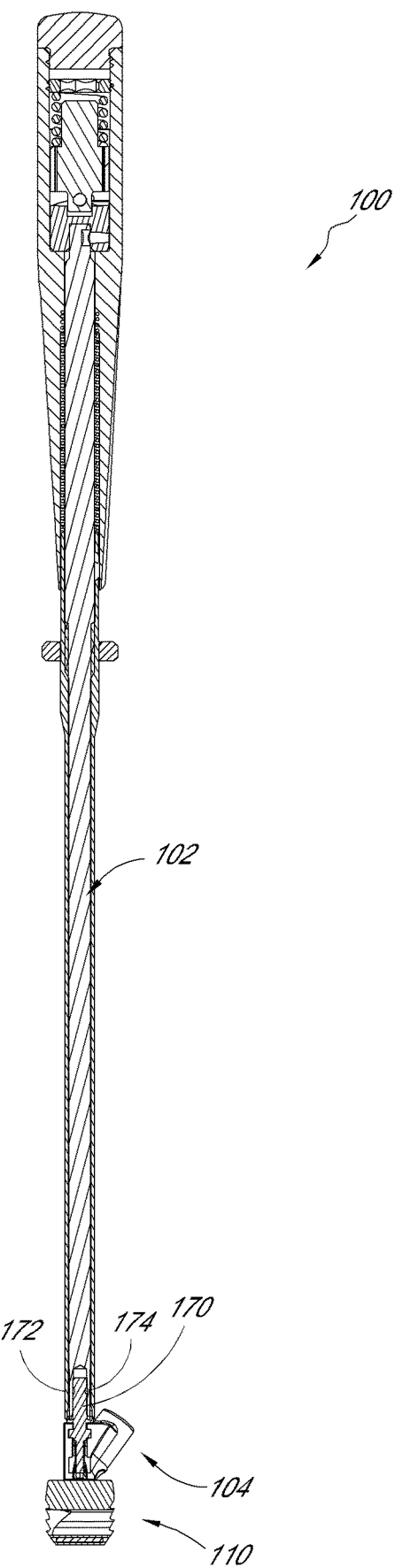
FIG. 13 is a cross-sectional view of the interbody implant inserter along line 13-13 of FIG. 1.

To facilitate attachment or engagement of the implant holder 104 and the handle 102, the implant holder 104 can include the engagement member 170. The engagement member 170 of the implant holder 104 is configured to be detachable coupled to a complementary engagement member 172 in the distal end of the handle 102 as shown in FIG. 13. The engagement member 170 and the complementary engagement member 172 provide a mechanical linkage from the handle 102 to the first portion 106 and the second portion 108 of the implant holder 104.

As shown in FIG. 13, the engagement member 170 can be centrally located on the implant holder 104. For instance, the engagement member 170 can be located approximately in between the first portion 106 and the second portion 108. The complementary engagement member 172 may be near the distal end of the handle 102. For instance, the complementary engagement member 172 can be an internal surface near the distal end of the handle 102.

As shown in FIG. 13, the engagement member 170 comprises a head 174. The head 174 can have a variety of cross-sectional shapes include hexagon, square, oval, etc. The complementary engagement member 172 can include a complementary socket. The head 174 and the socket can permit the transmission of torque between the handle 102 and the engagement member 170. Other configurations are contemplated.

In some embodiments, the engagement member 170 and complementary engagement member 172 can comprise, for example, any of a variety of complementary mechanical interfits, such as a threaded lock, snap-on fitting, or an interlocking fit. In some embodiments, the interfit may be a friction fit or a magnetic fit. In some embodiments, the complementary engagement member 172 may comprise a hook or detent that engages a recess or groove on the engagement member 170. In some embodiments, the complementary engagement member 172 may comprise a pivot or clamp member that retain the engagement member 170 by grasping onto the sides of the engagement member 170. One of skill in the art will understand that any of a variety of disengageable mechanisms known in the art may be used to detachably couple the handle 102 to the implant holder 104.

The interaction between the engagement member 170 of the implant holder 104 and the complementary engagement member 172 of the handle 102 facilitates attachment and detachment of the handle 102 from the implant holder 104. The quick release connection between the implant holder 104 and the handle 102 can allow easy attachment and detachment of the handle 102. This can be useful for x-ray imaging used during placement of the interbody implant 110. The engagement members 170, 172 may include a feature that prevents inadvertent detachment between the handle 102 and the implant holder 104, as in the embodiment illustrated in FIG. 8. For instance, this feature could include a detent and slot arrangement, a bayonet connection, snap fit or structure known in the art to prevent inadvertent detachment. The interaction between the engagement members 170, 172 provides a mechanical interlink between the handle 102 and implant holder 104. In some embodiments, the handle 102 may be permanently attached to the implant holder 104 (e.g., irremovable).

The handle 102 can be used with an impact hammer. The engagement member 170 can include a shoulder 216, as illustrated in FIG. 8. The proximal surface of the shoulder 216 can contact the handle 102. The distal surface of the shoulder 216 can contact the implant holder 104. The forces of the impact hammer can be transmitted from the handle 102, through the shoulder 216, through the implant holder 104 and to the interbody implant 110.

The design of the interbody implant inserter 100 reduces the need for the implant holder 104 to be held steady by the user during the drilling process. The implant holder 104 is fixedly received between the interbody implant 110 and the handle 102. This may facilitate implantation by not requiring holding of the implant holder 104 during the instrumentation process. The implant holder 104 can additionally detachably engage and disengage the interbody implant 110. This may be useful for manipulating interbody implant 110 that are small in size or difficult to access, by providing a larger structure for the user to manipulate during implantation. The implant holder 104 and handle 102 can then be detached once implantation is completed. The handle 102 can provide added maneuverability such that the user may position the interbody implant 110 more accurately.

C. Implantation Procedure

In some embodiments, the patient can be intubated and general anesthesia can be achieved. The patient can be prepped and draped in the usual sterile fashion. An anterior approach to the spine can be used to expose the anterior vertebral bodies. Many anterior approaches to the vertebral column are described in various medical texts such as Campbell's Operative Orthopaedics, 10th ed., edited by Canale et al., pp. 1569-1588, herein incorporated by reference. In some embodiments, the upper cervical spine can be accessed. The anterior upper cervical spine can be accessed by a transoral or retropharyngeal route, or by using a subtotal or extended maxillotomy. In other embodiments, the lower cervical spine, cervicothoracic junction, thoracic spine, thoracolumbar junction, lumbar region, lumbosacral junction, sacrum or combination of the above regions can be accessed. The intervertebral space can be debrided.

The interbody implant inserter 100 can be at least partially assembled. In some methods of use, the handle 102 is coupled to the implant holder 104 or 304. The engagement member 170 of the implant holder 104 can be received within the complementary engagement member 172 of the handle 102. The handle 102 can be mechanically coupled to the implant holder 104 such that rotation of the handle 102 or a portion thereof causes rotation of the engagement member 170. In some methods of use, the engagement member 170 is rotated by the handle 102. In some methods of use, the engagement member 170 is rotated by hand. The implant holder 304 can be coupled to the handle 102 in a similar manner.

The engagement member 170 is rotated causing the carrier 188 to translate along the engagement member 170. The carrier 188 interacts with the first portion 106 and the second portion 108 of the implant holder 104. The width between the first portion 106 and the second portion 108 can be increased or decreased by rotation of the engagement member 170. For instance, clockwise rotation of the engagement member 170 may cause the width to decrease and counterclockwise rotation of the engagement member may cause the width to increase. The implant holder 304 can be actuated by the handle 102 in a similar manner. The width between the first portion 306 and the second portion 308 can be increased or decreased by rotation of the engagement member 170, as shown in FIGS. 14-20.

The distance between the engagement sites 140 of the implant holder 104 can be increased or decreased by rotation of the engagement member 170. In some methods of use, the distance between engagement sites 140 can be increased. The interbody implant 110 can be inserted between the engagement sites 140. The distance between the engagement sites 140 can be decreased. Further rotation of the engagement member 170 can cause the engagement sites 140 of the implant holder 104 to engage the complementary engagement sites 142 of the interbody implant 110. In some embodiments, the first flange 144 of the first portion 106 engages the first protrusion 152 of the interbody implant 110. The second flange 146 of the second portion 108 engages the second protrusion 154 of the interbody implant 110. The engagement sites 140 clamp the interbody implant 110 placed there between. In some embodiments, the handle 102 is coupled to the implant holder 104 before the interbody implant 110 is clamped by the implant holder 104. In some embodiments, the handle 102 is coupled to the implant holder 104 after the interbody implant 110 is clamped by the implant holder 104. The implant holder 304 can be clamped in a similar manner. The distance between the engagement sites 340 of the implant holder 304 can be increased or decreased by rotation of the engagement member 170, as shown in FIGS. 14-20. FIG. 20 shows the internal mechanism including the carrier 188. FIG. 20 shows a removable shoulder 316 which couples to the engagement member 170.

In some methods of use, the first guide lumen 158 is aligned with the first hole 128 of the interbody implant 110 when the interbody implant 110 is clamped by the implant holder 104. The second guide lumen 160 is aligned with the second hole 130 of the interbody implant 110 when the interbody implant 110 is clamped by the implant holder 104. This alignment facilitates the placement of the fasteners through the drill guides 112, 114 and into the holes 128, 130. The implant holder 304 can be aligned in a similar manner. The first guide lumen 358 is aligned with the first hole 128 of the interbody implant 110 when the interbody implant 110 is clamped by the implant holder 304, see FIGS. 3 and 14-20. The second guide lumen 360 is aligned with the second hole 130 of the interbody implant 110 when the interbody implant 110 is clamped by the implant holder 304, see FIGS. 3 and 14-20.

In some embodiments, the interbody implant 110 can be packed with natural or artificial bone matrix and/or other osteogenesis factors. In some embodiments, the interbody implant 110 can be manipulated through a cannula to the implantation site. The cannula can have a diameter slightly larger than the implant holder 104. The interbody implant 110 can be inserted into an intervertebral space between the superior vertebra and the inferior vertebra. The superior surface 118 can be adjacent to the superior vertebra and the inferior surface 120 can be adjacent to the inferior vertebra. In some methods of use, the implant holder 104, 304 can be positioned in the intervertebral space. In some embodiments, the handle 102 is removed for placement of the fasteners. In some embodiments, the handle 102 remains coupled to the implant holder 104, 304 during placement of the fasteners.

One or more fasteners and/or one or more tools can be guided along the trajectories 12, 14 by the drill guides 112, 114. In some methods of use, the fasteners can be inserted through the cannula used to deliver the interbody implant 110. Each fastener can be coupled to a driver to facilitate insertion of the fastener into the bone. The guide lumen 158 of the first drill guide 112 guides the first fastener through the hole 128 in the interbody implant 110. In some embodiments, the guide lumen 158 of the first drill guide 112 guides the first fastener through the implant holder 104, the interbody implant 110, and into the superior vertebra. The guide lumen 160 of the second drill guide 114 guides the second fastener through the hole 130 in the interbody implant 110. In some embodiments, the guide lumen 160 of the second drill guide 114 guides the second fastener through the implant holder 104, the interbody implant 110, and into the inferior vertebra. The implant holder 304 can guide fasteners or tools in a similar manner. One or more fasteners and/or one or more tools can be guided along the trajectories 32, 34 by the drill guides 312, 314, see FIGS. 14-20. The guide lumen 358 of the first drill guide 312 guides the first fastener through the hole 128 in the interbody implant 110, see FIGS. 3 and 14-20. The guide lumen 360 of the second drill guide 314 guides the second fastener through the hole 130 in the interbody implant 110, see FIGS. 3 and 14-20.

Referring to FIGS. 1 and 14, the fastener can follow the axis 10 along the length of the handle 102 through the cannula toward the implantation site. The fastener can be manipulated such that the distal end is inserted into the first drill guide 112, 312. The fastener can follow the trajectory 12, 32 along the first drill guide 112, 312 toward the interbody implant 110. The trajectory 12, 32 can form the insertion angle 16, 36 with the axis 10. The insertion angle 16, 36 can be an acute angle (e.g., 5°, 10°, 15°, 20°, 25°, 30°, 35°, 40°, 45°, 50°, 55°, 60°, 65°, 70°, 80°, 85°, etc.). The trajectory 12 can guide the fastener into a vertebral body. In some embodiments, the trajectory 12 can guide the fastener into the superior vertebra.

The fastener can also follow the axis 10 along the length of the handle 102 through the cannula toward the implantation site. The fastener can be manipulated such that the distal end is inserted into the second drill guide 114, 314. The fastener can follow the trajectory 14, 34 along the second drill guide 114, 314 toward the interbody implant 110. The trajectory 14, 34 can form the insertion angle 18, 38 with the axis 10. The insertion angle 18, 28 can be an acute angle (e.g., 5°, 10°, 15°, 20°, 25°, 30°, 35°, 40°, 45°, 50°, 55°, 60°, 65°, 70°, 80°, 85°, etc.). In some embodiments, the insertion angles 16, 18 are the same. In some embodiments, the insertion angles 36, 38 are the same. The trajectory 14, 34 can guide the fastener into a vertebral body. In some embodiments, the trajectory 14, 34 can guide the fastener into the inferior vertebra. In some embodiments, the trajectories 12, 14 cross. In some embodiments, the trajectories 32, 34 cross.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the disclosed invention. For all the embodiments described above, the steps of the methods need not be performed sequentially. Thus, it is intended that the scope of the present invention herein disclosed should not be limited by the particular disclosed embodiments described above, but should be determined only by a fair reading of the claims that follow.

What is claimed is:

1. A method of using an implant inserter comprising a first portion having a first guide lumen and a second portion having a second guide lumen, an engagement member disposed between the first portion and the second portion, a carrier coupled to the engagement member and disposed between the first portion and the second portion, the method comprising:

translating the first portion of the implant inserter toward the second portion of the implant inserter to clamp an implant, wherein the carrier translates along the engagement member as the engagement member is rotated in a first direction, wherein translating the first portion of the implant inserter toward the second portion of the implant inserter aligns the first guide lumen with a first hole of the implant and aligns the second guide lumen with a second hole of the implant.

2. The method as in claim 1, further comprising implanting the implant with the implant inserter coupled thereto.

3. The method as in claim 1, further comprising inserting a fastener through the first guide lumen, the first hole, and into a superior vertebra.

4. The method as in claim 3, further comprising inserting a second fastener through the second guide lumen, the second hole, and into an inferior vertebra.

5. The method as in claim 4, further comprising translating the first portion of the implant inserter away from the second portion of the implant inserter to release the implant after inserting the first fastener and the second fastener.

6. The method as in claim 1, further comprising rotating the engagement member of the implant inserter to translate the first portion of the implant inserter away from the second portion of the implant inserter.

7. The method as in claim 1, further comprising visualizing a trajectory through the first portion via a slot in the first portion.

8. The method as in claim 7, further comprising visualizing a trajectory through the second portion via a slot in the second portion.

9. The method as in claim 1, further comprising abutting a stop with an anatomical structure to limit the depth of insertion of the implant.

\* \* \* \* \*